US005980861A

United States Patent [19]
Hnatowich et al.

[11] Patent Number: 5,980,861
[45] Date of Patent: Nov. 9, 1999

[54] CHELATOR COMPOSITIONS AND METHODS OF SYNTHESIS THEREOF

[75] Inventors: Donald J. Hnatowich, Brookline; Mary Rusckowski, Southborough; George Mardirossian, Worcester, all of Mass.; Paul Winnard, Jr., Holden, Me.; Fengchun Chang, Worcester, Mass.

[73] Assignee: University of Massachusetts, Worcester, Mass.

[21] Appl. No.: 08/614,078

[22] Filed: Mar. 12, 1996

[51] Int. Cl.$^6$ .......................... A61K 51/00; A61M 36/14
[52] U.S. Cl. .................... 424/1.69; 530/331; 424/1.11; 424/1.65; 424/1.73; 534/14
[58] Field of Search .................................. 424/1.11, 1.37, 424/1.53, 1.63, 1.73, 1.69, 9.1, 9.3, 9.34, 9.341, 9.351, 9.4, 9.42, 9.5; 530/300, 324–330, 331; 534/7, 10–16; 206/223, 569, 570; 536/22.1

[56] References Cited

U.S. PATENT DOCUMENTS

| | | | |
|---|---|---|---|
| 4,861,869 | 8/1989 | Nicolotti et al. | 530/402 |
| 5,082,930 | 1/1992 | Nicolotti et al. | 503/402 |
| 5,091,514 | 2/1992 | Fritzberg et al. | 534/14 |
| 5,144,043 | 9/1992 | Dean et al. | 548/548 |
| 5,218,128 | 6/1993 | Dean et al. | 548/546 |
| 5,534,497 | 7/1996 | Verbruggen | 514/18 |
| 5,541,287 | 7/1996 | Yau et al. | 530/317 |
| 5,556,982 | 9/1996 | Fritzberg et al. | 548/303.7 |
| 5,573,748 | 11/1996 | Fritzberg | 424/1.69 |
| 5,605,672 | 2/1997 | Bogdanov et al. | 424/1.65 |
| 5,616,692 | 4/1997 | Fritzberg et al. | 530/391.5 |

OTHER PUBLICATIONS

Fritzberg, A.R., "Advances in $^{99m}$Tc–Labeling of Antibodies," Nucl.–Med., vol. 26, 7–12, (1987).

Fritzberg, A. R. et al., "Approaches to Radiolabeling of Antibodies for Diagnosis and Therapy of Cancer," Pharmaceutical Research, vol. 5, No. 6, 325–334 (1988).

Fritzberg, A. R. et al., "Synthesis and Biological Evaluation of Tc–99m N,N'–Bis(mercaptoacetyl)–2,3–diaminopropanoate: A Potential Replacement for [$^{131}$I]o–iodohippurate," The Journal of Nuclear Medicine, vol. 23, No. 7, 592–598 (1982).

Ram, S. and Buchsbaum, D., "A Peptide–Based Bifunctional Chelating Agent for $^{99m}$Tc–and $^{186}$Re–Labeling of Monoclonal Antibodies," Cancer Supplement, vol. 73, No. 3, 769–773 (Feb. 1, 1994).

Abrams, Michael J. et al. (1990) "Technetium–99m–Human Ployclonal IgG Radiolabeled via the Hydrazino Nicotinamide Derivative for Imaging Focal Sites of Infection in Rats" The Journal of Nuclear Medicine 31(12):2022–2028.

Bos, Ebo S. et al. (1994) "In Vitro Evaluation of DNA–DNA Hybridization as a Two–Step Approach in Radioimmunotherapy of Cancer" Cancer Research 54:3479–3486.

Cazenave, Christian et al. (1987) "Rate of degradation of [α]–and [β]–oligodeoxynucleotides in Xenopus oocytes. Implications for anti–messenger strategies" Nucleic Acids Research 15(24):10506–10521.

Dewanjee, Mrinal K. (1993) "Radiolabeled Antisense Probes: Diagnosis and Therapy" Diagn Oncol 3:189–208.

Dewanjee, Mrinal K. et al. (1994) "Noninvasive Imaging of c–myc Oncogene Messenger RNA with Indium–111–Antisense Probes in a Mammary Tumor–Bearing Mouse Model" J. Nucl Med 35:1054–1063.

Dewanjee, Mrinal K. et al. (1994) "Labeling Antisense Deoxyologonucleotide with Tc–99m and Hybridization with c–myc Oncogene MRNA in P388 Leukemic Cells" J. of Labelled Compounds and Radiopharmaceuticals 35:40–42.

Ducan, R. Julian S. et al. (1983) "A New Reagent Which May Be Used to Introduce Sulfhydryl Groups into Proteins, and Its Use in the Preparation of Conjugates for Immunoassey" Analytical Biochemistry 132:68–73.

Egholm, Michael et al. (1992) "Peptide Nucleic Acids (PNA). Oligonucleotide Analogues with an Achiral Peptide Backbone" J. Am. Chem Soc. 114:1895–1897.

Egholm, Micheal et al. (1993) "PNA hybridizes to complementary oligonucleotides obeying the Watson–Crick hydrogenbonding rules" Nature 365:566–568.

Eisenhut, M. et al. (1996) "Bifunctional NHS–BAT Ester for Antibody Conjugation and Stable Technetium–99m Labeling: Conjugation Chemistry, Immunoreactivity and Kit Formation" J. of Nuclear Medicine 37:362–370.

Fritzberg, Alan R. (1986) "Synthesis and Biological Evaluation of Technetium–99m $MAG_3$ as a Hippuran Replacement" J Nucl Med 27:111–116.

Goldrosen, M. H. (1990) "Biodistribution, Pharmocokinetic, and Imaging Studies with $^{186}$Relabeled NR–LU–10 Whole Antibody in LS174T Colonic Tumor–bearing Mice" Cancer Research 50:7973–7978.

Gordon, Eric M. et al. (1994) "Application of Combinatorial Technologies to Drug Discovery. 2. Combinatorial Organic Synthesis, Library Screening Strategies, and Future Directions" J. of Medicinal Chemistry 37(10):1385–1401.

Hnatowich, D.J. et al. (1996) "Comparative Properties of a Technetium–99m–Labeled Single–Stranded Natural DNA and a Phosphorothioate Derivative in Vitro and in Mice" J. of Pharmacology and Experimental Therapeutics 276(1):326–334.

Hnatowich, D.J. et al. (1993) "Directly and Indirectly Technetium–99m–Labeled Antibodies—A Comparison of In Vitro and Animal In Vivo Properties" J. Nucl Med 34:109–119.

Hnatowich, D.J. et al. (1994) "Can a Cysteine Challenge Assay Predict the In Vivo Behavior of $^{99m}$Tc–labeled antibodies?" Nucl. Med. Biol. 21(8):1035–1044.

(List continued on next page.)

Primary Examiner—José G. Dees
Assistant Examiner—Dameron Jones
Attorney, Agent, or Firm—Lahive & Cockfield, LLP

[57] ABSTRACT

Compositions of radiolabeled nucleic acids and methods for synthesis and use thereof are disclosed.

8 Claims, 13 Drawing Sheets

OTHER PUBLICATIONS

Hnatowich, D.J. et al. (1995) "Technetium–99m Labeling of DNA Oligonucleotides" *J. of Nuclear Medicine 36*(12):2306–2314.

Wickstrom, Eric (1986) "Oligodeoxynucleotide Stability in Subcellular Extracts and Culture Media" *J. of Biochemical and Biophysical Methods 13*:97–102.

Winnard, P. Jr. and Hnatowich, D.J. (1995) "A method for the Facile Preparation of MAG3 Conjugated DNA–Used as an Alternative $^{99m}$TC Labeling Method to Avoid Nonspecific Protein Binding" Eleventh International Symposium on Radiopharmaceutical Chemistry, Vancouver, B.C. Canada (Aug. 13–17, 1995).

CHELATOR COMPOSITIONS AND METHODS OF SYNTHESIS THEREOF

GOVERNMENT FUNDING

Work described herein was supported under grants DE-FG02-93ER61656 from the U.S. Department of Energy. The U.S. government therefore may have certain rights in this invention.

BACKGROUND OF THE INVENTION

Oligonucleotides and polynucleotides are of interest for development of new products for diagnostics, imaging and therapy, due to their ability to hybridize specifically to oligonucleotides of complementary sequence. This property of single-stranded oligomers (i.e., to locate the complementary sequence and form a double-stranded molecule or a complex as a third strand) can be used to advantage in radiopharmaceutical development. For example, oligon, leotide DNAs are currently under investigation for antisense applications (Uhlmann E., Peyman A., Chem. Rev., 90: 543–584; 1990; and Dewanjee M. K., Diagn. Oncol., 3: 189–208, 1993.). If radiolabeled, these oligonucleotides may usefully deliver radioactivity to targeted cells or tissues. Recently, c-myc oncogene mRNA was targeted in mice with a radiolabeled antisense probe (Dewanjee M. K., Ghafouripour A. K., Kapakvanjwala M., Dewanjee S, Serafini A N, Lopez D M, Sfakinakis G N. J. Nucl. Med., 35: 1054–1063, 1994). Other possible applications include methods of radiolabeling large molecules by hybridization, pretargeting approaches based on oligonucleotides (Kuijpers W H A, Bos E S, Kaspersen F M, Veeneman G H, van Boeckel CAA., Bioconj. Chem., 4: 94–102; 1993) and the amplification of radioactivity within a tumor or other lesion by sequential administration of complementary DNAs (Hnatowich D. J., Winnard P. Jr., Virzi F. Fogarasi M., Sano T, Smith C L, Cantor C R, Rusckowski M., Proceedings, Fifth Conference on Radioimmunodetection and Radioimmunotherapy of Cancer, Princeton N.J., 1994).

Methods for labeling medically important macromolecules with metal radionuclides have been developed, but they have not yet proved generally useful because of limitations in various aspects of their use. The practitioner chooses a particular protein or nucleic acid on the basis of its properties of affinity for a particular target in a biological system, and this affinity is the basis for that molecule's potential as a therapeutic or diagnostic composition. The labeling method must preserve the native structure of that molecule to assure that the binding function is not substantially reduced. Further, the potential use is enhanced if the radionuclide as supplied to the macromolecule is not substantially further transferred to miscellaneous cells or serum proteins, causing diminishment of radioactivity delivered to a target site, and increased non-specific background radiation. The ability to retain the radiolabel is a function of several factors, including the stability of the macromolecule to endogenous enzymes, possible chemical compromise to its structural integrity following the labeling procedure, and the nature of the chemical bond between the macromolecule and the radiolabel.

Proteins have been labeled with technetium-99m ($^{99m}$Tc) using the hydrazino nicotinamide (SHNH) chelator (Abrams M. J., Juweid M., tenKate C. I., Schwartz D. A., Hauser M. M., Gaul F. E., Fuccello A. J., Rubin R. H., Strauss H. W., Fischman A. J, J. Nucl. Med., 31: 2022–2028, 1990) and the label found to be stable in vitro and in vivo (Hnatowich D. J., Mardirossian G., Ruscowski M., Fogarasi M, Virzi F, Winnard P Jr., J. Nucl. Med., 34; 109–119, 1993). The SHNH chelator was initially used for oligonucleotides, however, transfer of label nonspecifically to proteins from oligonucleotides labeled in this manner was observed. The identical oligonucleotide; radiolabeled with $^{111}$In using the chelator diethylenetriamine-pentaacetic acid (DTPA) showed no tendency to bind to serum proteins under circumstances in which the $^{99m}$Tc-SHNH-labeled oligonucleotide was largely protein bound (Hnatowich D. J., Winnard P. Jr., Virzi F, Fogarasi M, Sano T, Smith C L, Cantor C R, Rusckowski M., J. Nucl. Med., 36: 2306–2314, 1995). This nonspecific protein binding can be attributed to use of the SHNH chelator for coupling the nucleic acid to $^{99m}$Tc.

The N-[N-[N-[(benzoylthio)acetyl]glycyl]glycyl]glycine (MAG$_3$) chelator of $^{99m}$Tc was originally developed as an alternative to radiolabeled hippuran for renal function studies (Fritzberg A R., Kasina S., Eshima D., Johnson D. L., J. Nucl. Med., 27: 111–116; 1986). This succinimide ester mercapto-acetyl tripeptide is protected against disulfide-bond formation by a benzoyl group, which must be heated to 100° C. for 10 min during labeling to remove the protecting group. This benzoyl-protected chelator has also been used to radiolabel antibodies with $^{99m}$Tc (Fritzberg A. R., Berninger R. W., Hadley S. W. et al., Pharmaceutical Res., 5: 325–334; 1988) and radiorhenium (Goldrosen M H., Biddle W C., Pancook S. Bakshi S., Vanderheyden J-L., Fritzberg A. R., Morgan A. C., Foon K. A., Cancer Res., 50: 7973–7978; 1990). However, past use of the chelator for protein labeling has been limited since the benzoyl protecting group requires extreme alkaline pH or boiling temperatures for sulfur deprotection. The MAG$_3$ chelator has also been used to label antibodies by post-conjugation methods through the use of an isophthaloyl group for protection in place of the benzoyl group (Weber R. W., Boutin R. H., Nedelman M. A., Lister-James J., Dean R. D., Bioconjug. Chem 1:431–437, 1990). However, in addition to a complicated synthesis, this approach requires an additional step (deprotection) and the immediate labeling of the deprotected-conjugated antibody before disulfide bond formation can occur in solution. Accordingly, this chelator has been radiolabeled prior to conjugation (i.e. preconjugation labeling) with macromolecular polymers such as proteins or polypeptides, which cannot withstand harsh conditions. Preconjugation labeling can be a complex procedure with multiple intermediate purification steps. More importantly from the point of view of application of radionuclide-labeled macromolecules for diagnostics, imaging and therapeutics, preconjugation labeling limits the usefulness of the product: the preconjugation radionuclide-chelator complex has a short half-life, cannot be transported without necessary precautions for radioactivity, and exposes end-users to radioactivity during a number of complex synthetic steps, all required prior to end use with samples or patients.

SUMMARY OF THE INVENTION

This invention provides compositions and methods for radiolabeling procedures that can be accessed immediately prior to end use.

The invention provides a composition comprising a nucleic acid selected from the group consisting of a peptide nucleic acid or a ribonucleic acid, a chelator moiety, and a radionuclide, wherein the chelator moiety is covalently linked to the nucleic acid, and the radionuclide binds to the chelator moiety. In a preferred embodiment, the radionuclide is selcted from the group consisting of technetium-93m, technetium-95m, technetium-99m, rhenium 186, rhenium 188 and rhenium 189. In the most preferred embodiment, the radionuclide is technetium-99m. In one embodiment, the nucleic acid of the composition is a ribonucleic acid. In a preferred embodiment, the nucleic acid of the composition is a peptide nucleic acid. In certain embodiments, the nucleic acid may comprise at least one nonnaturally occurring or unusual base.

In a preferred embodiment, the composition wherein the peptide nucleic acid or the ribonucleic acid is covalently bound to the chelator moiety occurs through a nitrogen atom that is provided on the nucleic acid. The nitrogen atom is preferably linked to a terminal residue of the peptide nucleic acid, for example the C or N terminus, or to the 5' or 3' terminus of ribonucleic acid.

In a preferred embodiment,the chelator moiety preferably is a tetradentate chelator. More preferably, the chelator moiety is an oligopeptide chelator, and most preferably the chelator moiety is a tripeptide. Preferably, the chelator moiety further comprises a sulfur atom, and in the most preferred embodiment the tripeptide comprises glycine or serine residues.

The invention also provides a composition comprising an activated ester of an acetyl-protected mercaptoacetyl oligopeptide chelator. In a preferred embodiment of this composition, the activated ester is an N-hydroxysuccinimide ester. In certain preferred embodiments, the activated ester of an acetyl-protected mercaptacetyl oligopeptide is triglycine or triserine. Accordingly, the invention features the composition comprising acetyl-N-[N-[N-mercaptoacetyl]-glycyl]glycyl]glycine or acetyl-N-[N-[N-mercaptoacetyl]-seryl]seryl]serine. In a preferred embodiment, the nucleic acid is complementary to nucleic acid encoding a tumor-specific DNA sequence.

The invention provides a composition comprising a nucleic acid selected from the group consisting of a peptide nucleic acid or a ribonucleic acid, and a chelator moiety; wherein the chelator moiety is covalently linked to the nucleic acid. In one embodiment of the invention, the chelator moiety comprises a sulfur atom, and the sulfur atom is protected by a protecting group of the formula —C(O)-lower alkyl.

The invention also features a pharmaceutical composition comprising a peptide nucleic acid-chelator-radionuclide complex and a pharmaceutically acceptable carrier.

In another aspect, the invention provides a method of synthesizing an activated ester of an S-protected mercaptoacetyl amino acid, comprising the steps of reacting an amino acid with an activated ester of an S-protected thioglycolic acid under conditions such that an S-protected mercaptoacetylamino acid and an activating alcohol are formed, and reacting the S-protected mercaptoacetylamino acid and the activating alcohol with a coupling reagent under conditions such that an activated ester of an S-protected mercaptoacetyl amino acid is formed. A preferred embodiment of this method features dicyclohexylcarbodiimide as the coupling reagent. A more preferred embodiment features providing additional activating alcohol for the second part of the reaction in the presence of the coupling reagent. In another aspect of the preferred embodiment of this method, the amino acid is an oligopeptide, and in the most preferred embodiment, the oligopeptide is a tripeptide. Further, the oligopeptide in the method comprises residues of amino acids selected from the group consisting of glycine, serine, proline, alanine, and phenylalanine. In the preferred embodiment, the oligopeptide is triglycine or triserine.

In another aspect, the invention provides a method for forming a polymer-chelator-radionuclide complex, comprising the steps of contacting a polymer-chelator compound with a radionuclide under mild conditions, and allowing a polymer-chelator-radionuclide complex to form, wherein the polymer-chelator compound is selected from the group consisting of protein-chelators and nucleic acid-chelators. In this method, the radionuclide is preferably technetium-99m, which preferably is provided in the form of a pertechnetate. In certain embodiments, the method further comprises contacting the pertechnetate with a reducing agent. In a preferred embodiment, the chelator is a mercaptooligopeptide chelator.

In another aspect, the invention provides a method for detecting a tumor, comprising the steps of administering to a patient a composition of of a radionuclide-chelator-peptide nucleic acid in a pharmaceutically acceptable carrier, and detecting a radioactive signal to detect a tumor. In a preferred embodiment, the method further comprises converting the radioactive signal to generate an image of a tumor.

The invention features a kit comprising an antibody-chelator or a binding protein-chelator in a container, wherein the chelator comprises a sulfur atom protected by a protecting group of the formula —C(O)-lower alkyl, and instructions for complexing the antibody-chelator or binding protein-chelator with a radionuclide under mild conditions. In one embodiment of this kit, the antibody-chelator or binding protein-chelator specifically binds to a tumor-specific gene product.

In another aspect, the invention provides a method for diagnosis of an infectious disease, comprising the steps of treating a sample from a patient with a peptide nucleic acid-chelator-radionuclide composition, wherein said composition has affinity for a nucleic acid sequence or a gene product of an infectious agent, such that the composition complexes to the nucleic acid sequence or the gene product, and detecting the composition complexed to the infectious agent or to a gene product of the infectious agent.

In another aspect, the invention provides a method for imaging sites of an infection, comprising the steps of administering to a patient a peptide nucleic acid-chelator-radionuclide composition in a pharmaceutically acceptable carrier, wherein said composition has affinity for nucleic acid sequence or a gene product of an infectious agent, such that the composition complexes to the infectious agent, and detecting the composition complexed to the infectious agent.

In another aspect, the invention provides a method of treating a solid tumor, comprising the steps of administering to a patient in need thereof a high specific activity preparation of a composition of claim 5 in a pharmaceutically acceptable carrier to a site proximal to a tumor, and allowing the radio-labeled complex to accumulate at the tumor site and destroy the tumor cells.

Yet another feature of the invention is a method of treating an infectious disease, comprising the steps of administering a high specific activity preparation of radionuclide-chelator-nucleic acid or radionuclide-chelator-binding protein composition in a pharmaceutically acceptable carrier to a site proximal to the infection, and allowing the radiolabeled complex to accumulate at the site of the infection, such that the infectious disease is treated.

The invention also provides a kit comprising a peptide nucleic acid-chelator in a container, and instructions for complexing with a radionuclide. One preferred embodiment of this kit features the peptide nucleic acid being complementary to a tumor-specific nucleic acid. In a different preferred embodiment, the kit features peptide nucleic acid which is complementary to nucleic acid of a pathogenic organism selected from one of the group of pathogenic bacterial species, pathogenic fungal species, pathogenic viral species, or pathogenic protozoal species.

DETAILED DESCRIPTION OF THE INVENTION

Figure 1:
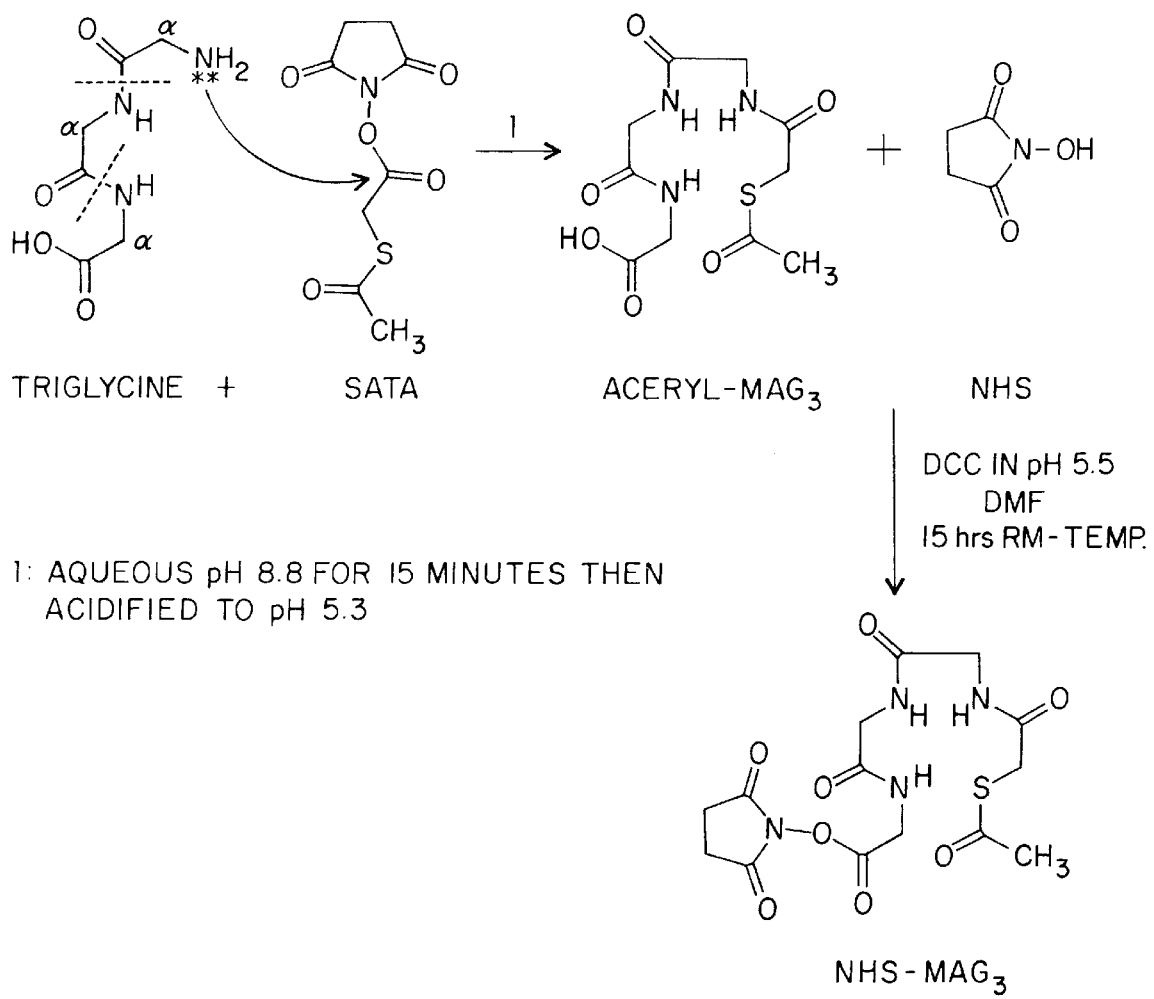
FIG. 1 is a scheme showing a synthesis of acetyl-protected NHS-MAG$_3$.
Figure 2A:
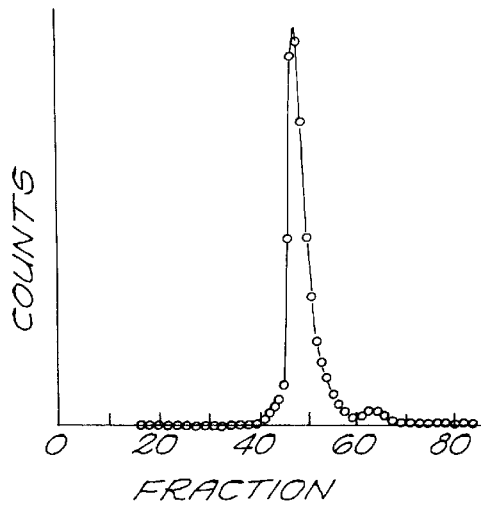
FIG. 2 depicts radiochromatograms obtained by size exclusion HPLC analysis. Panel A: of $^{99m}$Tc-MAG$_3$-DNA; Panel B: after adding the radiolabeled DNA to biotin saturated avidin; Panel C: after adding the radiolabeled DNA to unsaturated avidin; Panel D: after adding the radiolabeled DNA to avidin to which the complementary DNA was previously bound.
Figure 2B:
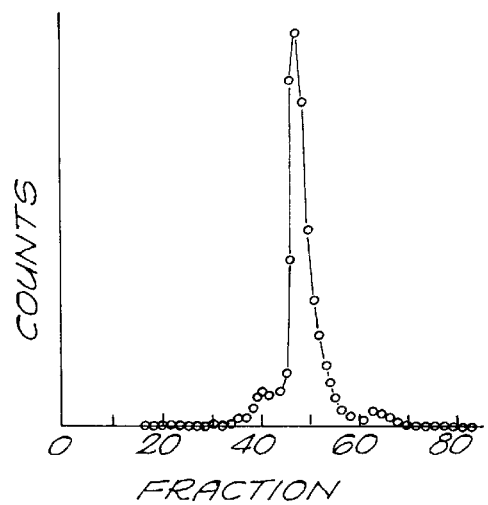
Figure 2C:
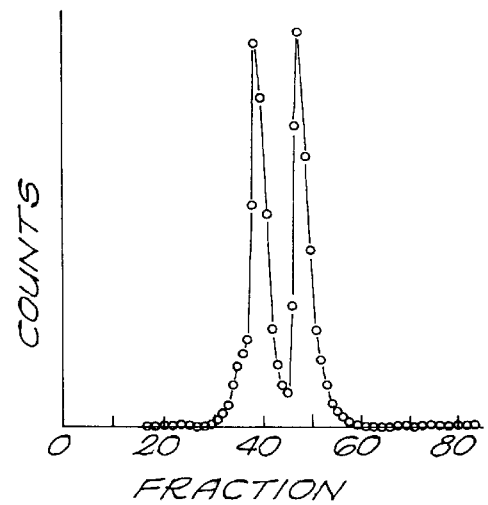
Figure 2D:
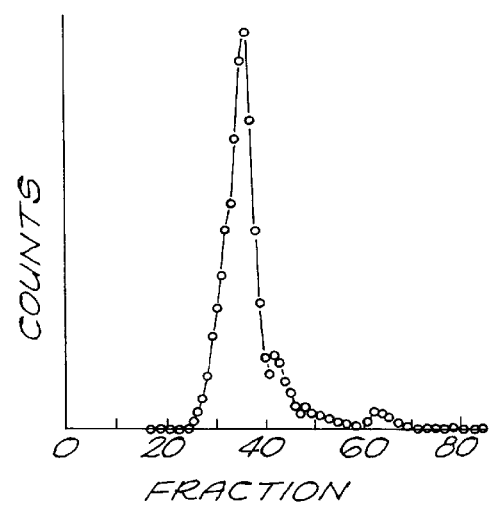

Other aspects of this invention consider nucleotides that are alternatives to naturally occuring deoxynucleic acid with its sugar-phosphate backbone, or synthetic oligo- and polynucleotide sugar-phosphate polymers. Initially the native single-stranded phosphodiester DNA has been considered for these, and other, in vivo applications, these unmodified oligonucleotides are highly susceptible to degradation by nucleases (Wickstrom E. *J. Biochem Biophys Methods.* 13:97–102, 1986; Cazenave C., Chevrier M., Ngugent T, Helene C. *Nucleic Acids Res.* 15:10507–10521, 1987; Ceruzzi M. Draper K. *Nucleosides Nucleotides* 8: 815–818, 1989) and, as such may be an inappropriate carrier of radioactivity for in vivo imaging, diagnostic and therapeutic applications. Methods have been developed to chemically modify the phosphodiester DNA to improve its stability (Goodchild J. *Bioconj. Chem.* 1: 165–187, 1990). Among the many possible modified DNAs, the most popular at present is the phosphorothioate, in which a nonbonding oxygen in the phosphate backbone is replaced with a sulfur (Iversen P. In *Antisense research and applications*, Crooke S T, Lebleu B. eds. CRC Press, Ann Arbor Mich., 1993 p462–469). Data from investigations of a phosphorothioate DNA radiolabeled with $^{99m}$Tc indicate however that there is a high affinity for serum and tissue proteins and resulting unfavorable pharmacokinetics (Hnatowich D J, Mardirossian G, Fogarasi M, Sano T, Smith C L, Cantor C R, Rusckowski M, Winnard P. Jr. *Pharm Exp Therap* 276: 326–334; 1996.).

For convenience, certain terms employed in the specification, examples and appended claims are collected here.

The term "radionuclide", as used herein, refers to a radioactive isotope of a selected element, preferrably a metallic element. Preferred radionuclides include isotopes of technetium and rhenium, and more preferably the isotopes technetium-93m, technetium-95m, technetium-99m, rhenium 186, rhenium 188 or rhenium 189. In a most preferred embodiment, the radionuclide is technetium-99m, particularly in the form of Tc(O)$^{3+}$. Technetium-99m has a half-life of 6.0 hours and an energy of decay of 0.14 MeV (Handbook of Chemistry and Physics, CRC Press, 64th edition, 1983), and has been widely used for in vivo and in vitro labeling studies and diagnostic applications.

The term "patient," as used herein, refers to an animal in need of treatment or diagnosis for, or susceptible to, conditions characterized by the presence or absence of specific nucleic acid sequences, e.g., cancer or infectious disease. In preferred embodiments, the subject is a mammal, including humans and non-human mammals such as dogs, cats, pigs, cows, sheep, goats, rats, and mice. In a particularly preferred embodiment, the subject is a human.

As used herein, the term "nucleic acid molecule" is intended to include DNA molecules (e.g., cDNA or genomic DNA), RNA molecules (e.g., mRNA), and analogs of DNA, such as peptide nucleic acid molecules (PNA), phosphorothioate DNA, and DNA based on a peptide analog backbone such as a trans-olefin peptidomimetics and phosphonate peptidomimetics. Peptide nucleic acid (PNA) is an oligomer in which the charged phosphateribose backbone has been eliminated and replaced with an uncharged polyamide backbone (Egholm M., Buchardt O., Nielsen P E., Berg R H., *J. Am. Chem. Soc.*, 114: 1895–1897; 1992). These oligomers have been reported to resist nuclease and protease degradation (Egholm M., Buchardt O., Christensen L., Behrens C., Freier S M., Driver D A., Berg R H., Kim S K., Norden B., Nielsen P E., *Nature*, 365: 566–568; 1993.). Furthermore, the binding affinities of PNA for its complementary single-stranded PNA has been shown to exceed that of comparable DNAs (Egholm M., Buchardt O., Nielsen P E., Berg R H., *J. Am. Chem. Soc.*, 114: 1895–1897; 1992).

A nucleic acid molecule may be single-stranded or double-stranded, but preferably is single-stranded. In preferred embodiments, the nucleic acid is PNA or RNA, and most preferably is PNA.

As used herein, a "naturally-occurring" nucleic acid molecule refers to an RNA or DNA molecule having a nucleotide sequence that occurs in nature, whether it is prepared by isolation from an organism or is chemically synthesized. A nucleic acid may be chemically synthesized using a commercially available automated synthesizer and reagents, or custom made by a commercial supplier (for example, PerSeptive Biosystems, Framingham, Mass.). A "chimeric nucleic acid" is a covalently link of a first base sequence with a second base sequence of different chemical character, for example, a PNA strand covalently linked to a DNA or RNA strand. An "isolated" nucleic acid molecule is free of sequences which naturally flank the nucleic acid (i.e., sequences located at the 5' and 3' ends of the nucleic acid) in the genomic DNA of the organism from which the nucleic acid is derived. For example, in various embodiments, an isolated tumor-specific nucleic acid molecule may contain less than about 5 kb, 1 kb, 0.5 kb, 0.1 kb or 50 bases of nucleotide sequences which naturally flank the nucleic acid molecule in genomic DNA of the cell from which the nucleic acid is derived (e.g. a human brain tumor). Moreover, an "isolated" nucleic acid molecule, such as an RNA molecule, may be free of other cellular material. The nucleic acid molecule may comprise only a portion of a coding region of a naturally occurring sequence.

In a preferred embodiment, an isolated nucleic acid molecule of the invention comprises a base nucleotide sequence with a specific linear order of the bases adenine, guanine, cystosine, thymine or uracil, or modified derivatives of these bases (e.g., methyladenine, and hydroxymethyluracil). A nucleic acid can contain non-naturally occurring bases, such as 5-fluorouracil, or "unusual" bases, such as ribothymidine or others, e.g., such as are found in tRNA. Other modified bases are known to those with skill in the art. The term "unusual base," as used herein, refers to uncommon bases such as pseudouracil or ribothymine, found, e.g., in tRNA.

It is also possible to modify the structure of the oligonucleotides and polynucleotides for such purposes as enhancing therapeutic or prophylactic efficacy, or stability (e.g., ex vivo shelf life and resistance to nucleolytic degradation in vivo). Exemplary modified nucleic acids and nucleic acid analogs include PNA and phosphorothioate-linked nucleic acids. Such modified nucleotides are considered functional equivalents of the compositions described in more detail herein.

A nucleic acid molecule having a known nucleotide sequence can be isolated using standard molecular biology techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor, N.Y.). For example, mRNA can be isolated from cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon knowledge of the nucleotide sequence or fragments of the sequence, as will be appreciated by those with skill in the art.

In certain embodiments, an isolated nucleic acid molecule useful in the compositions and methods of the invention is at least 12 nucleotides in length and hybridizes under stringent conditions to a nucleic acid molecule comprising the nucleotide sequence of interest. In other embodiments, a nucleic acid is at least 15, 20, 30, 50, or 100 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that at least sequences at least 65%, more preferably at least 70%, and even more preferably at least 75% homologous to each other typically remain hybridized to each other. Such stringent conditions are known to those skilled in the art and can be found, e.g.,in *Current Protocols in Molecular Biology*, John Wiley & Sons, N.Y. (1989), 6.3.1–6.3.6. A preferred, non-limiting example of stringent hybridization conditions is hybridization in 6× sodium chloride/sodium citrate (SSC) at about 45° C., followed by one or more washes in 0.2× SSC, 0.1% SDS at 50–65° C. Preferably, an isolated nucleic acid molecule of the invention that hybridizes under stringent conditions to a sequence of the invention corresponds to a naturally-occurring nucleic acid molecule.

The term "can be degraded in vivo", as used herein, refers to a bond that can be cleaved in vivo, either enzymatically or non-enzymatically. For example, natural nucleic acids can be cleaved by nucleases that attack the sugar-phosphate backbone, at any phosphodiester bond or at specific sites.

In addition to nucleic acid molecules with sequences of interest, the invention contemplates use of nucleic acid molecules which are antisense thereto. An "antisense" nucleic acid comprises a nucleotide sequence which is complementary to a "sense" nucleic acid, e.g., complementary to the coding strand of a double-stranded cDNA molecule or complementary to an mRNA sequence. Antisense constructs of the present invention, by antagonizing the normal biological activity of tumor-specific or infectious DNA can be used in the therapeutic context, both to deliver a therapeutic dose of radionuclide, and to inhibit expression of tumor-specific or infectious genetic information. In a preferred embodiment, antisense nucleic acid can deliver a radionuclide complexed to a chelator covalently linked to the nucleic acid, to the target cells, tissue or sample.

Antisense nucleic acids can be designed according to the rules of Watson and Crick base pairing. The antisense nucleic acid can be complementary to an entire coding strand, or to only a portion thereof. In one embodiment, an antisense nucleic acid molecule is antisense to a "coding region" of the coding strand of a nucleotide sequence. The term "coding region" refers to the region of the nucleotide sequence comprising codons which are translated into amino acid residues. In another embodiment, the antisense nucleic acid molecule is antisense to a "noncoding region" of the coding strand of a nucleotide sequence of interest. The term "noncoding region" refers to 5' and 3' sequences which flank a coding region and are not translated into amino acids (i.e., also referred to as 5' and 3' untranslated regions). Antisense nucleic acid may be complementary to either or both of a coding region and an adjacent noncoding region.

The antisense nucleic acid molecule may be complementary to an entire coding region, but more preferably is an oligonucleotide which is antisense to only a portion of a coding or noncoding region. For example, an antisense oligonucleotide may be complementary to the region surrounding the translation start site of an mRNA. An antisense oligonucleotide can be, for example, about 15, 20, 25, 30, 35, 40, 45 or 50 nucleotides in length. An antisense nucleic acid of the invention can be constructed using chemical synthesis and/or enzymatic reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., peptide nucleic acid or phosphorothioate nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid).

As used herein, the term "polymer" is intended to include molecules formed by the chemical union of two or more combining subunits called monomers. Monomers are molecules or compounds which usually contain carbon and are of relatively low molecular weight and simple structure. A monomer can be converted to a polymer by combination with itself or other similar molecules or compounds. A polymer may be composed of a single identical repeating subunit or multiple different repeating subunits (copolymers). Polymers within the scope of this invention include substituted and unsubstituted oligopeptides, carbohydrates, polypeptides, oligonucleotides, polynucleotides, and polypeptide backbones substituted with purine and pyrimidine bases or base analogs (PNA).

The term "peptide" includes two or more amino acids covalently attached through a peptide bond. Amino acids which can be used in peptide molecules include those naturally occurring amino acids found in proteins such as glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. The term amino acid further includes analogs, derivatives and congeners of naturally occurring amino acids, one or more of which can be present in a peptide derivative. For example, amino acid analogs can have lengthened or shortened side chains or variant side chains with appropriate functional groups. Also included are the D and L stereoisomers of an amino acid when the structure of the amino acid admits of stereoisomeric forms. The term "peptide derivative" further includes compounds which contain molecules which mimic a peptide backbone but are not amino acids (so-called peptidomimetics), such as benzodiazepine molecules (see e.g. James, G. L. et al. (1993) Science 260:1937–1942). An oligopeptide can be designed to interact with a cell membrane constituent (e.g., if comprised primarily of hydrophobic amino acids). Accordingly, in one embodiment, an oligopeptide comprises three or four peptide residues, and a polypeptide comprises four or more residues. Polymers comprising oligopeptides or peptide backbones may be covalently linked to other moieties or functionalitites, for example, to an amine group attached via a linking arm.

The term "alkyl", as used herein, refers to a straight or branched chain hydrocarbon group having from about 1 to about 20 carbon atoms. The term "lower alkyl" refers to an alkyl group having from 1 to 6 carbon atoms. Exemplary lower alkyl groups include methyl, ethyl, n-propyl, isopropyl, n-butyl, isobutyl, sec-butyl, tert-butyl, n-pentyl, and n-hexyl. A $C_1$–$C_3$ alkyl refers to an alkyl group having 1 to 3 carbon atoms. An alkyl group may be unsubstituted, or may be substituted at one or more positions. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Preferred alkyls are lower alkyls.

The term "antibody" as used herein is intended to include fragments thereof which are also specifically reactive with one of the imaging, diagnostic and therapeutic targets. Antibodies can be fragmented using conventional techniques and the fragments screened for utility in the same manner as described above for whole antibodies. For example, $F(ab)_2$ fragments can be generated by treating an antibody with pepsin. The resulting $F(ab)_2$ fragment can be treated to reduce disulfide bridges to produce Fab fragments. The term "antibody" is further intended to include single chain, bispecific and chimeric molecules. The term "antibody" includes possible use both of monoclonal and polyclonal antibodies (Ab) directed against a target, according to the requirements of the application.

Polyclonal antibodies can be obtained by immunizing animals, for example rabbits or goats, with a purified form of the antigen of interest, or a fragment of the antigen containing at least one antigenic site. Conditions for obtaining optimal immunization of the animal, such as use of a particular immunization schedule, and using adjuvants e.g. Freund's adjuvant, or immunigenic substituents covalently attached to the antigen, e.g. keyhole limpet hemocyanin, to enhance the yield of antibody titers in serum, are well-known to those in the art,. Monoclonal antibodies are prepared by procedures well-known to the skilled artisan, involving obtaining clones of antibody-producing lymphocyte, i.e. cell lines derived from single cell line isolates, from an animal, e.g. a mouse, immunized with an antigen or antigen fragment containing a minimal number of antigenic determinants, and fusing said clone with a myeloma cell line to produce an immortalized high-yielding cell line. Many monoclonal and polyclonal antibody preparations are commercially available, and commercial service companies that offer expertise in purifying antigens, immunizing animals, maintaining and bleeding the animals, purifying sera and IgG fractions, or for selecting and fusing monoclonal antibody producing cell lines, are available.

Specific binding proteins with high affinities for targets can be made according to methods known to those in the art. For example, proteins that bind specific DNA sequences may be engineered (Ladner, R. C., Guterman, S. K., Ley, A. C., Kent, R. B., U.S. Pat. No. 5,096,815), and proteins that bind a variety of other targets, especially protein targets (Ladner, R. C., Guterman, S. K., Roberts, B. L., Markland, W., Ley, A. C., and Kent, R. B. U.S. Pat. No. 5,233,409; Ladner, R. C., Guterman, S. K., Roberts, B. L., Markland, W., Ley, A. C., and Kent, R. B. U.S. Pat. No. 5,403,484) may be engineered and used in the present invention for covalent linkage to a chelator molecule, so that a complex with a radionuclide may be formed under mild conditions. Antibodies and binding proteins can be incorporated into large scale diagnostic or assay protocols that require immobilizing the compositions of the present invention onto surfaces, for example in multi-well plate assays, or on beads for column purifications.

The term "chelator", as used herein, refers to a moiety that is capable of binding a radionuclide, preferably through non-covalent interactions, e.g., through ionic interactions. Chelator moieties suitable for use in the compositions and methods of the invention are preferably capable of binding to a radionuclide with a high affinity, e.g., a binding affinity sufficiently high to permit binding of a radionuclide, preferably under physiological conditions, e.g., in vivo. The term "nucleic acid-chelator" refers to a compound comprising a nucleic acid, including PNA, covalently bound to a chelator moiety. Similarly, "protein-chelator" refers to a protein, including an antibody, covalently bound to a chelator moiety.

Chelators which bind to radionuclides are known in the art, see, e.g., M. Nicolini et al., eds., "Technetium and Rhenium in Chemistry and Nuclear Medicine," SGEditoriali, Padova (1995). In general, preferred chelators are capable of binding to radionuclides such as $Tc(O)^{3+}$. In a preferred embodiment, a chelator moiety will be a tetradentate chelator, i.e., will be capable of four-point binding to a radionuclide. Exemplary tetradentate chelators include $N_2S_2$ and $N_3S$ chelators, as described in, e.g., A. R. Fritzberg, et al., J. Nucl. Med. 23:592–598 (1982); S. Liu and D. S. Edwards, in M. Nicolini et al., eds., "Technetium and Rhenium in Chemistry and Nuclear Medicine," op. cit., pp. 383–393; and S. Vallabhajousula et al., J. Nucl. Med. 30:599–604 (1989). An $N_2S_2$ chelator can chelate a radionuclide through two nitrogen atoms (e.g., amido nitrogens, e.g., of a peptide backbone) and two sulfur atoms (e.g., of a mercaptoacetyl moiety), while $N_3S$ chelators can chelate to a radionuclide through three nitrogen atoms and one sulfur atom.

Accordingly, preferred chelator moieties include amidothiols, including, e.g., mercaptoacetyltripeptides, such as, e.g., mercaptoacetyltriglycine ($MAG_3$), mercaptoacetyltriserine, and the like. Mercaptoacetyltripeptides can chelate radionuclides such as $Tc(O)^{3+}$ by coordination through the three amide nitrogens of the peptide backbone, and the terminal mercapto group. Other chelator moieties which may find use in the present invention include cyclams, porphyrins, crown ethers, azacrown ethers, and the like. As the skilled artisan will understand from the teachings herein, a chelator moiety will preferably be capable of covalently bonding to a nucleic acid, e.g., RNA or PNA, or other polymer compound. Thus, a mercaptoacetyltripeptide molecule can form an amide bond, e.g., through the C-terminal carboxyl moiety of the tripeptide, with a nitrogen atom of the nucleic acid. Similarly, a mercaptoacetyltripeptide can form an ester bond to a nucleic acid through an oxygen atom of the nucleic acid. The chelator moiety can be covalently linked to the nucleic acid through covalent bonds to other functionalities of the chelator moiety. For example, a mercaptoacetyltripeptide which includes an aspartate residue can form an ester or amide bond to a nucleic acid through the side-chain carboxylate of the aspartate residue.

The term "protecting group" is known in the art and refers to a moiety which blocks reaction at a particular atom or reactive center. A "protected" compound is a compound in which at least one atom is blocked by a protecing group. Thus, an "S-protected" compound includes a sulfur atom that is blocked with a protecting group.

The term "activated ester", as used herein, refers to an ester moiety suitable for use in a coupling reaction, e.g., to produce an ester or amide bond. A variety of activated esters are known in the art, see, e.g., G. A. Grant, Ed., "Synthetic Peptides: A User's Guide", W. H. Freeman, New York (1992), Chp.3, and M. Bodansky, "Principles of Peptide Synthesis", 2nd ed., Spring-Verlag (1993). In general, an activated ester suitable for use in the present invention will be sufficiently stable to permit storage of the ester for a suitable period of time before coupling to a nucleic acid. A preferred activated ester is an N-hydroxysuccinimide (NHS) ester, which is readily available from inexpensive starting reagents, see, e.g., example 2, infra.

Similarly, the term "activating alcohol," as used herein, refers to an alcohol or hydroxyl-containing compound which, when esterified with a carboxylate, forms an activated ester. Exemplary activated alcohols include N-hydroxysuccinimide, pentafluorophenol, HOBt, and the like.

The term "coupling reagent", as used herein, refers to a reagent capable of effecting coupling of, e.g., an amine and a carboxylate, to form an amide, or an alcohol and a carboxylate to form an ester. Coupling reagents are known in the art, see, e.g., M. Bodansky, "Principles of Peptide Synthesis", 2nd ed., supra.

As used herein, the term "mild conditions" refers to reaction conditions that do not result in significant degradation of destruction of a nucleic acid-chelator-radionuclide or protein-chelator-radionuclide composition. Thus, mild conditions generally include reaction in aqueous or aqueous-organic solution, at a pH range of about 5.5 to about 8.5, more preferably about 6 to about 8. Mild conditions also generally provide temperatures less than 100° C., more preferably less than 80° C., and still more preferably less than 60° C. Conditions appropriate for a particular reaction will be dependent on the nature of the composition and the reagents. For example, an antibody-chelator composition may be unstable above a temperature of about 45° C. due to denaturation of the antibody portion. Thus, mild conditions for radiolabeling an antibody-chelator compound may include a temperature no greater than 45° C., more preferably less than 40° C.

I. Compositions

In one aspect, the invention provides a composition comprising a peptide nucleic acid or ribonucleic acid, a chelator covalently linked to the peptide nucleic acid or ribonucleic acid, and a radionuclide bound to the chelator. Such compositions are useful for, e.g., diagnosis or treatment of, e.g., cancer or infectious diseases, as is described in more detail infra.

In general, the peptide nucleic acid or ribonucleic acid will be selected to be complementary to a sequence of interest, e.g., a diagnostic sequence. While the peptide nucleic acid or ribonucleic acid need not be perfectly complementary to the sequence of interest, in preferred embodiments, complementarity will be sufficient to permit hybridization to the sequence of interest, either in vitro or in vivo, while substantially excluding non-specific hybridization to other sequences. In preferred embodiments, the nucleic acid is perfectly complementary to a sequence of interest.

The chelator moiety can be linked to the nucleic acid moiety directly, e.g., through an atom of the nucleic acid moiety, or through a linking moiety. For example, a chelator can be linked to the nucleic acid moiety through an atom of the backbone, e.g., a terminal amine of a PNA or an oxygen atom, e.g., of a 3'- or 5'-terminal hydroxyl group, of an RNA. The nucleic acid moiety can be modified, e.g., by addition of an amine group, to facilitate attachment of the chelator moiety. Thus, for example, DNA or RNA which has been chemically modified to have a terminal amine group (which can be synthesized, or purchased from commercial sources, e.g., Operon Technologies, Alameda, Calif.) can be used to provide compositions of the invention. Alternatively, a chelator moiety can be linked to a nucleic acid base, e.g., a purine, a pyrimidine or a modified base, of a PNA or RNA moiety. In general, it is preferred to attach the chelator moiety to the PNA or RNA so as to substantially preserve the ability of the PNA or RNA to bind to its complementary strand. In general, attachment will be at a terminal residue of the nucleic acid moiety. Linking moieties can be selected to permit the covalent attachment of the nucleic acid moiety to the chelator moiety without steric hindrance between the two moieties, while not significantly disturbing the ability of the nucleic acid strand to bind its complement. Suitable linking moieties are known in the art and selection of a linking moiety will be routine to the skilled artisan.

In a preferred embodiment, the ratio of chelator moiety to nucleic acid moiety is 1:1, i.e., there is one chelator moiety bound to each oligonucleotide or oligopeptide nucleic acid moiety. However, in certain embodiments, it may be preferred to attach more than one chelator moiety to a nucleic acid moiety. For example, higher levels of radioactivity can be achieved by chelating several radionuclide moieties to each nucleic acid moiety through a plurality of chelating moieties. Also, several different radionuclides can be associated with one nucleic acid chain by using a plurality of chelating moieties per nucleic acid; thus, several therapeutic or diagnostic radionuclides can be employed with a single nucleic acid moiety. In compositions that include a plurality of chelator moieties, the chelator moieties can all be the same or can be different. The nucleic acid-chelator-radionuclide compositions of the invention can further comprise a group capable of specific bonding to a binding partner complement. Exemplary binding moieties include biotin, avidin or streptavidin, an antigen, an antibody, a receptor, a ligand, and the like. A nucleic acid-chelator-radionuclide composition derivatized with a binding moiety can be bound, e.g., to a solid support, by contacting with the complement to the binding moiety. Thus, a biotin binding group can be bound by avidin or streptavidin, or a derivative such as biocytin, which can be bound to a solid surface, e.g., a bead or a 96-well plate. For instance, biotinylated polymers can be prepared from biotin-NHS (N-hydroxy-succinimide) using techniques well known in the art (e.g., biotinylation kit, Pierce Chemicals, Rockford, Ill.), and the compositions immobilized in the wells of streptavidin-coated 96 well plates (Pierce Chemical). Exemplary methods for detecting such complexes include enzyme-linked assays, which rely on detecting an enzymatic activity associated with an enzyme activity linked to streptavidin or bound to streptavidin via an antibody. Illustratively, a polypeptide can be chemically cross-linked or genetically fused with alkaline phosphatase, and the amount of bound polypeptide trapped in the complex can be assessed with a chromogenic substrate of the enzyme, e.g. paranitrophenylphosphate. The addition of a binding group permits the ready isolation or purification of the nucleic acid complex from solution. Conveniently, biotinylated compounds can be readily immobilized for studying the in vitro binding or other properties of the nucleic acid-chelator or nucleic acid-chelator-radionuclide compositions of the invention. A chelator-protein composition can also be immobilized utilizing conjugation of biotin and streptavidin, or the like.

The choice of nucleic acid (e.g., DNA, RNA, or PNA) and chelator moiety will generally be guided according to at least some of the following criteria: 1) minimal non-specific binding in vitro or in vivo (e.g., little binding to serum proteins and the like); 2) ability to bind to specific nucleic acid sequences, e.g., diagnostic sequences, in vitro and in vivo; 3) stable complexation to a radionuclide; and 4) ease of synthesis. Thus, in preferred embodiments, a nucleic acid-chelator-radionuclide complex will bind to specific nucleic acid sequences, in vivo or in vitro, with relatively little non-specific binding, and the radionuclide will remain complexed under physiological conditions. The ability of a nucleic acid to bind to a complement, the extent of non-specific binding, and the binding affinity of the radionuclide for the chelator moiety can be assessed according to methods known in the art or described herein.

In another embodiment, the invention provides a composition comprising a peptide nucleic acid or ribonucleic acid, and a chelator moiety covalently linked to the peptide nucleic acid or ribonucleic acid. Such compositions are useful, e.g., for synthesizing nucleic acid-chelator-radionuclide compositions such as are described above.

In preferred embodiments, the chelator moiety is a mercaptoacetyl tripeptide, i.e., a tripeptide covalently linked (preferably at the amine terminus) to a mercaptoacetyl moiety, i.e., —C(O)—CH$_2$SR, wherein R is hydrogen or a protecting group. In preferred embodiments, the mercapto group is protected, preferably as a lower alkyl thioester, e.g., —S—C(O)-lower alkyl, prior to chelation with the radionuclide. The protecting group can prevent undesired side reactions at the sulfur atom, e.g., oxidation, during synthesis or storage of the nucleic acid-chelator compound. Protecting groups for sulfur are known (see, e.g., T. Greene and P. Wuts, "Protective Groups in Organic Synthesis," J. Wiley, (1991)). In preferred embodiments, the sulfur protecting group can be removed under mild conditions to unveil the free mercapto group, which can then participate in chelation of a radionuclide, e.g., Tc(O)$^{3+}$. Advantageously, a sulfur protecting group that can be removed under mild conditions allows the chelation of a radionuclide to the nucleic acid-chelator compound concomitant with removal of the protecting group, reducing the number of synthetic steps required and simplifying the experimental conditions. Thus, for example, an S-acetyl protecting group can be removed under conditions used for reduction of pertechnetate to Tc(O)$^{3+}$, e.g., in the presence of SnCl$_2$ at near neutral pH (see Example 4, infra), simultaneously generating a chelatable form of the radionuclide and the chelator moiety, and permitting chelation to occur.

In another embodiment, the invention provides a composition comprising a peptide nucleic acid covalently linked to an amidothiol chelator moiety, e.g., a chelator moiety comprising at least one amido nitrogen and at least one sulfur which can chelate to a radionuclide. In preferred embodiments, the amidothiol chelator moiety is a dipeptide or oligopeptide derivatized with a sulfur-containing moiety, e.g., a mercaptoacetyl moiety, such that the amidothiol chelator moiety can complex a radionuclide, e.g., in a teatradentate complex. In a particularly preferred embodiment, the amidothiol chelator moiety is a mercaptoacetyltripeptide.

In another embodiment, the invention provides a kit comprising a peptide nucleic acid-chelator compound in a container, and instructions for complexing with a radionuclide. In preferred embodiments, the peptide nucleic acid is complementary to a tumor-specific nucleic acid. In preferred embodiments, the peptide nucleic acid is complementary to nucleic acid of a pathogenic organism selected from one of the group of pathogenic bacterial species, pathogenic fungal species, pathogenic viral species, or pathogenic protozoal species. In certain preferred embodiments, the chelator moiety is an amidothiol chelator. Such kits are useful for the synthesis of radiolabeled compositions.

In another aspect, the invention provides a kit comprising an antibody-chelator or a binding protein-chelator in a container, wherein the chelator comprises a sulfur atom protected by a protecting group of the formula —C(O)-lower alkyl (more preferably an acetyl group), and instructions for complexing the antibody-chelator or binding protein-chelator with a radionuclide under mild conditions. In preferred embodiments, the antibody-chelator or binding protein-chelator specifically binds to a tumor-specific sequence or a tumor-specific gene product. In preferred embodiments, the nucleic acid may carry the sequence complementary to tumor-specific DNA, which includes DNA from one of the class consisting of oncogenes, tumor promoters, tumor suppressors, cancer predisposition genes such as mutated Wilm's tumor or BrcA, or tumor marker genes.

In another embodiment, the invention provides libraries of chelator compounds, libraries of nucleic acid-chelators, and libraries of nucleic acid-chelator-radionuclides. Such libraries can be synthesized according to methods for combinatorial synthesis (see infra). Libraries of chelators, nucleic acid-chelator compounds, and nucleic acid-chelator-radionuclides are useful for rapidly screening for compounds with desired properties, e.g., low non-specific binding, selected lipophilicity, high or low affinity for radionuclides, and the like.

In a preferred embodiment, a library of chelator compounds comprises at least 10, more preferably at least 25, more preferably at least 50, more preferably at least 100, and still more preferably at least 500 different chelator compounds. In preferred embodiments, a library of nucleic acid-chelator compounds comprises at least 10, more preferably at least 25, more preferably at least 50, more preferably at least 100, and still more preferably at least 500 different nucleic acid-chelator compounds. In preferred embodiments, a library of nucleic acid-chelator-radionuclides complexes comprises at least 10, more preferably at least 25, more preferably at least 50, more preferably at least 100, and still more preferably at least 500 different nucleic acid-chelator-radionuclide complexes.

II. Methods of the Invention

In one aspect, the invention provides a method of synthesizing an activated ester of an S-protected mercaptoacetyl amino acid comprising the steps of (a) reacting an amino acid with an activated ester of an S-protected thioglycolic acid under conditions such that an S-protected mercaptoacetylamino acid and an activating alcohol are formed; and (b) reacting the S-protected mercaptoacetylamino acid and the activating alcohol with a coupling reagent under conditions such that an activated ester of an S-protected mercaptoacetyl amino acid is formed.

In preferred embodiments, the amino acid is an oligopeptide, more preferably a tripeptide, still more preferably triglycine. In certain preferred embodiments, the activated ester of S-acetylthioglycolic acid (SATA) is the N-hydroxysuccinimide (NHS) ester of S-acetylthioglycolic acid. In preferred embodiments, the activated ester of the S-protected mercaptoacetyl amino acid is an N-hydroxysuccinimide ester. In preferred embodiments, the coupling reagent is a carbodiimide, more prefereably dicyclohexylcarbodiimide. In preferred embodiments, the S-protected thioglycolic acid is SATA, e.g., the protecting group on sulfur is an acetyl group. In other preferred embodiments, the sulfur protecting group has the formula —C(O)-lower alkyl. In a preferred embodiment, step (b) includes the further step of providing additional activating alcohol to the reaction mixture formed in step (a). in a preferred embodiment, the activating alcohol is N-hydroxysuccinimide.

The amino acid is preferably contacted with the activated ester of S-acetylthioglycolic in solution. In preferred embodiments, the solvent is a polar aprotic solvent, although any solvent capable of solubilizing the reactants without causing or participating in undesired side reactions can be used. Exemplary solvents include dimethylformamide (DMF), dichloromethane, dimethylacetamide, dioxane, tetrahydrofuran, ether, dimethoxyethane, and the like, or mixtures thereof. Reaction times will generally be in the range of 0.25–24 hours; progress of the reaction can be monitored by standard techniques, e.g., HPLC, thin-layer chromatography, NMR spectroscopy, and the like. The reactions can be performed at temperatures ranging from about 0° C. to about 100° C., more preferably about 10° C. to about 60° C., and more preferably about 15° C. to about 40° C. The reactions can also be performed under anhydrous conditions and inert atmosphere, e.g., of nitrogen or argon.

The method preferably includes the further step of purifying the S-protected mercaptoacetyl amino acid. Purification can be by a variety of means known in the art, including chromatographic methods such as flash chromatography, HPLC, or gel filtration chromatography.

The method provides advantages over known methods of synthesis of S-protected mercaptoacetyl amino acids. The synthesis requires only two steps, which can be performed in one pot, preferably without isolation or purification of intermediates. Thus, the inventive method is simple and rapid, and can provide high yields of the desired compounds. Furthermore, the starting materials (e.g., the NHS ester of SATA) are commercially available and are inexpensive. Activated esters of S-protected mercaptoacetyl amino acids can be used as protected chelator moieties for synthesis of radionuclide-labeled molecules, e.g., macromolecules such as nucleic acids (including peptide nucleic acids), antibodies, polypeptides, carbohydrates, hormones, and the like. In many cases, covalent attachment of the chelator moiety to the target molecule (e.g., a macromolecule) can be easily and selectively achieved through methods known in the art for coupling of molecules with activated esters.

In another aspect, the invention provides a method of synthesizing a macromolecule-chelator-radionuclide complex. The method includes the steps of contacting a macromolecule-chelator compound (e.g., macromolecules including nucleic acids (preferably PNA), proteins or polypeptides (e.g., antibodies) or carbohydrates) with a radionuclide under mild conditions, and allowing a macromolecule-chelator-radionuclide complex to form. In preferred embodiments, the macromolecule is a nucleic acid, e.g., a DNA, an RNA, or a PNA, more preferably a peptide nucleic acid. In preferred embodiments, the chelator moiety is a tetradentate chelator, more preferably an amidothiol, yet more preferably an oligopeptid-ethiol, and still more preferably a tripeptide-thiol. A preferred chelator moiety is mercaptoacetyltriglycyl. In preferred embodiments, the radionuclide is technetium-99m.

In preferred embodiments, the contacting step occurs under conditions suitable for formation of a macromolecule-chelator-radionuclide complex. Thus, the radionuclide can be supplied in the form of a chelate, e.g., a tartrate complex, which can undergo transchelation with the macromolecule-chelator to form a macromolecule-chelator-radionuclide complex. Alternatively, the radionuclide can be supplied in a form which requires further treatment, e.g., reduction, to a chelatable form. In an exemplary embodiment, the method includes the step of contacting the radionuclide with a reducing agent to provide the radionuclide in a chelatable form. Thus, for example, pertechnetate can be reduced to Tc(V) (e.g., Tc(O)$^{3+}$), which is then complexed by the chelator moiety. Preferred reducing agents include SnCl$_2$ and other reducing agents capable of reducing an oxidized radionuclide to a chelatable oxidation state, preferably under mild conditions.

In another aspect, the invention provides methods for synthesizing libraries of chelator compounds. In another aspect, the invention provides methods for synthesizing libraries of nucleic acid-chelator compounds. In another aspect, the invention provides methods for synthesizing libraries of nucleic acid-chelator-radionuclide complexes.

The synthesis of combinatorial libraries is well known in the art and has been reviewed (see, e.g., E. M. Gordon et al., *J. Med. Chem.* 37:1385–1401 (1994)). The subject invention contemplates methods for synthesis of combinatorial libraries of chelator compounds, nucleic acid-chelator compounds, and nucleic acid-chelator-radionuclide complexes. Such libraries can be synthesized according to a variety of methods. For example, a "split-pool" strategy can be implemented in the following way: beads of a functionalized polymeric support (e.g., a resin for peptide synthesis, e.g., Merrifield resin) are placed in a plurality of reaction vessels. To each aliquot of beads is added a solution of a different chelator (e.g., different tripeptides), and the reactions proceed to yield a plurality of solid-supported chelator compounds. The aliquots of derivatized beads are then washed, "pooled" (i.e., recombined), and the pool of beads is again divided, with each aliquot being placed in a separate reaction vessel. To each reaction vessel is added a solution of a different S-protected thioglycolic acid (i.e., differently S-protected), and reaction occurs to yield a plurality of reaction vessels each containing a plurality of S-protected mercaptoacetylchelator compounds, which can then be released from the solid support and screened, e.g., for lipophilicity, ease of removal of the protecting group, and the like.

Other synthesis methods, including the "diversomer library" synthesis of Hobbs DeWitt et al. (*Proc. Natl. Acad. Sci. U.S.A.* 90:6909 (1993)) or the "tea-bag" technique of Houghten (see, e.g., Houghten et al., *Nature* 354:84–86 (1991)) can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J. Med. Chem.*, op. cit.). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, calorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

Combinatorial libraries of compounds can also be synthesized with "tags" to encode the identity of each member of the library (see, e.g., W. C. Still et al., PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In another aspect, the invention provides a method of forming a polymer-chelator-radionuclide complex, comprising the steps of (a) contacting a polymer-chelator compound with a radionuclide under mild conditions; and (b) allowing a polymer-chelator-radionuclide complex to form; wherein the polymer-chelator compound is selected from the group consisting of protein-chelators and nucleic acid-chelators. In preferred embodiments, the radionuclide is technetium-99m. In preferred embodiments, the technetium-99m is provided in the form of a pertechnetate. In preferred embodiments, the method comprises further contacting the pertechnetate with a reducing agent. In a particularly preferred embodiment, reduction of the radionuclide and chelation of the reduced radionuclide occur in a single step, e.g., concomitantly. In preferred embodiments, the chelator is a mercaptooligopeptide chelator. in preferred embodiments, the nucleic acid-chelator is a peptide nucleic acid-chelator.

III. Pharmaceutical Compositions

The compounds of the invention can be incorporated into pharmaceutical compositions suitable for administration to a subject. In a preferred embodiment, the pharmaceutical composition comprises either a peptide nucleic acid-radionuclide-chelator complex of the invention or a radionuclide-chelator complex of the invention and a pharmaceutically acceptable carrier.

In yet another embodiment of the present invention, the pharmaceutical composition polypeptide can be administered by combination therapy, i.e., combined with other agents. For example, the combination therapy can include a composition of the present invention with at least one anti-cancer or at least one antibiotic. Exemplary anti-cancer agents include cis-platin, adriamycin, and taxol. Exemplary antibiotics include isoniazid, rifamycin, and tetracycline.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Depending on the route of administration, the active compound may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1–19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The compounds can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. The concentration of the compound in the compositions and preparations may, of course, be varied. The amount of compound in such therapeutically useful compositions is selected such that a suitable therapeutic dosage is obtained.

To administer a compound of the invention by other than parenteral administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the composition which produces a therapeutic effect. Generally, out of one hundred per cent, this amount will range from about 0.01 percent to about ninety-nine percent of active ingredient, preferably from about 0.1 percent to about 70 percent, most preferably from about 1 percent to about 30 percent.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A composition of the present invention may also be administered as a bolus, electuary or paste.

Liquid dosage forms for oral administration of the compositions of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compositions, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of compositions of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to a composition of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present therapeutic inventions to the body. Such dosage forms can be made by dissolving or dispersing the composition in the proper medium. Absorption enhancers can also be used to increase the flux of the composition across the skin. The rate of such flux can be controlled by either providing a rate controlling membrane or dispersing the composition in a polymer matrix or gel. Devices, including patches, which transdermally deliver a composition by iontophoresis or other electrically-assisted methods can also be employed in the present invention, including, for example, the devices described in U.S. Pat. Nos. 4,708,716 and 5,372,579.

Ophthalmic formulations, eye ointments, powders, solutions, drops, sprays and the like, are also contemplated as being within the scope of this invention.

Pharmaceutical compositions of this invention suitable for parenteral administration comprise one or more composition of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc.; administration by injection, infusion or inhalation; topical by lotion or ointment; and rectal by suppositories. Injection (subcutaneous or intraperitoneal) is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, administered perferably proximal to the site of the target. For example, for imaging of a cancer of the gastro-intestinal tract, oral administration to an unfed subject or patient is appropriate, while intravenous administration is appropriate for imaging of the urinary tract. Intraspinal administration is appropriate for imaging of the brain and central nervous system. The compounds of this invention for a patient, when used as an imaging agent, are preferred to be administered in the range of 0.1 milliCuries per kg of body weight to about 10 milliCuries per kilogram of body weight per day, more preferably from about 1 milliCurie per kg to about 4 milliCuries per kg.

If desired, the effective daily dose of a therapeutic compositions may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4.,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In a preferred embodiment, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on the unique characteristics of the therapeutic compound and the particular therapeutic effect to be achieved, and the limitations inherent in the art of compounding such a therapeutic compound for the diagnosis, imaging, or treatment of tumors or infectious diseases in subjects.

A "therapeutically effective dosage" preferably inhibits tumor growth or pathogen infection by at least about 20%, more preferably by at least about 40%, even more preferably by at least about 60%, and still more preferably by at least about 80% relative to untreated subjects. The ability of a compound to inhibit cancer or infectious disease can be evaluated in an animal model system that may be predictive of efficacy in human tumors and infectious diseases. Alternatively, this property of a composition can be evaluated by examining the ability of the compound to inhibit, such inhibition in vitro by assays well-known to the skilled practitioner.

A therapeutically effective amount of a therapeutic compound can decrease tumor size, prevent or delay death of infected tissues or organs, decrease fever and white cell count, or otherwise ameliorate symptoms in a subject. One of ordinary skill in the art would be able to determine such amounts based on such factors as the subject's size, the severity of the subject's symptoms, and the particular composition or route of administration selected.

In the compositions of the present invention, the PNA and RNA moieties of the invented compositions are preferably chemically synthesized. However RNA is also available from biological sources, for example, produced in reasonably high yields from a recombinant organism in which the RNA is transcribed by a high activity promoter. In this manner either the sense strand or the antisense strand is obtained, according to the objectives of the skilled artisan who is practicing this invention. Whether the source of the nucleic acid is from chemical synthesis or a biological sample, the material is preferably single stranded, and purification methods known to the skilled artisan, for example acrylamide gel electrophoresis or column chromatography for example on a P4 column (BioRad, Melville, N.Y.), are used to obtain isolated nucleic acids for coupling to the chelator of the invention. Covalent linkage of the chelator molecule is achieved by coupling via an amine attached to the terminal phosphate group through a 6-member methylene carbon spacer. Attachment of a biotin moiety, if appropriate (*J. Nuclear Med.* 36: 2306–2314), is achieved directly through a 15-member amide-polyether to the terminal phosphate. Other entities that would enhance the therapeutic function of the nucleic acid are similarly linked to a terminus of the nucleic acid, for example a member of the cytokine class of proteins such as epidermal growth factor, platelet-derived growth factor, and nerve growth factor.

The invention comprises a variety of tripeptide tetradentate chelators, composed of combinations of the amino acids gly, ser, ala, leu, ile, phe, val, pro, met, phe and thr, offer the user of the invention an array of chelators which embody a variety of desired characteristics, and is not limited to any one amino acid moiety. The $MAG_3$ entity, for example, is even more stable in vivo, as it is exemplified in the example below, so that a smaller proportion of the radionuclide is transferred non-specifically to serum proteins. Greater in vivo stability produces greater contrast as an imaging agent between the target tumor or site of infection, or organ to be imaged such as the kidney, and the background of non-target tissues. A greater therapeutic index is obtained, i.e., fewer side effects due to destruction of normal tissue, are observed if nonspecific transfer or loss of the radionuclide metal occurs. Further, choice of an amino acid with a large hydrophobic side chain, such as phenylalanine, for the oligopeptide chelator synthesis for example $MAG_3$, enables the user to custom design properties such as cell permeation, so that the imaging and therapeutic aspects of the tripartite composition of matter are further enhanced.

The invention provides a method for detecting a tumor, comprising the steps of administering to a patient a radionuclide-chelator-peptide nucleic acid composition in a pharmaceutically acceptable carrier, and detecting a radioactive signal to detect a tumor. In the preferred mode of the invention, the PNA sequence of this method is complementary to a tumor-specific sequence that is uniquely expressed in the tumor. As described infra, such a sequence may be in an oncogene, a mutated tumor suppressor gene, a form of a gene that confers predisposition to a cancer, or a gene for a protein marker that appears on a tumor. Examples of these are well-known to those skilled in the art, and a few of those are given here for the purposes of illustration, but not with the intent of limiting the present invention to these examples.

The nestin protein, which is expressed in normal mammalian foetal development, is again expressed on tumors of the central nervous system, including most forms of brain cancer (McKay, D. G. Ronald, U.S. Pat. No. 5,338,839, Aug. 16, 1994). It is also expressed on melanomas and on metastasized melanomas (V. A. Florenes, R. Holm, O. Myklebost, U. Lendahl, O. Fodstad, *Cancer Res.* 54: 354–6, 1994), found in other tissues and difficult to detect or treat, in fact rendering metastasized melanoma difficult to detect and cure. The methods of this invention include administration of, for example, PNA with a sequence complementary to the mRNA of the nestin protein, preferably to the unique portion of the human nestin gene, will direct the radionuclide-chelator-PNA composition to the location of the brain tumor, or to the metastasized melanoma cells, and localize the radioactivity to these sites. The preferred site of delivery is within the central nervous system or directly to the brain via spinal injection or fine needle delivery, and the tumors may be imaged in equipment standard at a clinical nuclear medicine facility, for example, a whole body scanner (Siemans). Most preferably, the whole body scanner is equipped with computing equipment and software, such as a Harris Computer Center with multiple terminals permitting programming and the use of data reduction programs. The radioactivity accumulating a specific sites in the body can be converted to images of the tumor with the associated software. Methods and routes for detection of nestin DNA sequence information for brain cancer can be applied to diagnostics and imaging of meningiomas, another pathological condition associated with the nervous system, using data available on the identification and characterization of genes differentially expressed in mengiomas (M. Murphy, M. J. Pykett, P. Harnish, K. D. Zang, D. L. George, *Cell Growth Differ* 4:715, 1991).

Other tumor types for which the methods of this invention are applicable include, but are not limited to, Wilm's tumor (A. J. Buckler, K. M. Call, T. M. Glaser, D. A. Haber, D. E. Housman, C. Y. Ito, J. Pelletier, Rose, E. A. Rose, U.S. Pat. No. 5,350,840,), a pediatric kidney cancer due to a somatic mutation in the patient's single copy of a gene normally found in two intact copies. Wilm's tumor can be cured surgically in 95% of cases, but an imaging agent is appropriate for monitoring remission, and for detection and imaging of newly appearing tumors. Other examples of known cancer-associated DNA sequences for which the compositions of matter and methods of the current invention are suitable include those associated with gastrointestinal cancer (R. Fishel, R. D. Kolodner, R. A. G. Reenan, R. A. Reenan, World Patent No. WO 95/14085, May 26, 1995), those associated with appearance of multiple drug resistance during chemotherapy (J. M. Croop, P. Gros, D. E. Housman, U.S. Pat. No. 5,198,344), and a large number of classical oncogenes such as Rb, ras, c-myc and neu, the sequences of which are available for analysis to those with skill in the art.

The inventive compositions and methods for diagnosis, imaging and therapeutic applications are tools to be used in combination with standard medical compositions and methods, such as surgery and chemotherapy and radiation therapy for treating cancer. Further, the inventions of this application, while described as diagnostic or therapeutic, may in fact serve both purposes, for example a therapeutic dose of radionuclide also serves as a composition to monitor the course of therapy. For example, accumulation of radiolabel at a site of a tumor or an infection can be monitored for maintenance of size and shape over the course of the therapy without necessity of a separate dosage merely for diagnostic imaging. The known half-life of the radionuclide predicts a time at which the labeling density will decline to half of that of the initial reading. A concomitant decrease in size of the tumor or infected site can be used to track the effectiveness of the treatment, as can a decline in label density at a rate faster than that of the half-life of the radionuclide.

Similarly, the compositions and methods of the current invention are useful for diagnostics, imaging and for therapeutic agents for infectious diseases of humans, animals and plants. The term "infectious disease" is meant to include disorders caused by one or more species of bacteria, viruses, fungi, and protozoans, which are disease-producing organisms are collecively referred to as "pathogens." In this invention, pathogens are exemplified, but not limited to, *Mycobacterium tuberculosis, M leprae, Pseudomonas aeruginosa, Shigella dysenteria, Salmonella typhi, S. paratyphi, Streptococcus hemolyticus, Hemophilus pneumoniae, Escherichia coli* serotype 0157, Chlamydia species, Helicobacter species; HIV-1,-2, and -3, HSV-I and -II, non-A non-B, non-C hepatitis virus, pox viruses, rabies viruses, Aspergillus species, *Entamoeba histolytica, Giardia species, Erwinia carotovora,* cauliflower mosaic virus, and Newcastle disease virus. Obtaining unique sequences from these organisms by screening available data bases and by performing hybridizations in vitro are commonly known to those skilled in the art (see, e.g., Ladner et al, U.S. Pat. No. 5,096,815, Mar. 17,1992).

In compositions of this invention, the nucleotide sequences of interest can be complementary to tumor-specific mRNA (or to a unique sequence from a pathogen), so that the nucleic acid of the composition is doubly functional as a "homing" or delivery molecule for the target tumor or infected cells, but also may possess a therapeutic function in that it forms a stable complex with the naturally occuring mRNA, or with genomic DNA to inhibit transcription.

The specific activity pertains to the ratio of molecules of composition bearing technetium-99m to the total number of molecules of the composition. The high coupling efficiencies described in the examples below indicate that specific activity of the radionuclide is sufficiently high for use in significant radioactive quantity.

EXEMPLIFICATION

The invention now being generally described, it will be more readily understood by reference to the following examples which are included merely for purposes of illustration of certain aspects and embodiments of the present invention, and are not intended to limit the invention.

The chelator N-[N-[N-[(benzoylthio)acetyl]glycyl] glycyl]glycine (benzoyl $MAG_3$) has been used successfully to radiolabel proteins and other molecules with technetium-99m and radiorhenium. Prior to radiolabeling, the sulfur in this mercaptotripeptide chelator is protected by a benzoyl leaving group which requires extreme alkaline pH or boiling temperatures for deprotection. As a result, the benzoyl-protected chelator is radiolabeled prior to conjugation (i.e. preconjugation labeling) in the case of carriers such as proteins or polypeptides which cannot withstand harsh conditions. The examples below teach a one-pot, two-step, synthesis of the N-hydroxysuccinimide derivative of acetyl-$MAG_3$ (NHS-$MAG_3$) with commercially obtained reagents. Furthermore, because in the invention here a different protecting group (acetyl) is used which is more easily removed, good labeling efficiencies with technetium-99m can be achieved rapidly at nearneutral pH and at room temperature. The technetium-99m labeled $MAG_3$-DNA was evaluated for stability in comparison to the same DNA radiolabeled with technetium-99m via a different chelator, the hydrazino nicotinamide (SHNH) chelator. The radiolabel in these complexes was found to be similarly stable to transchelation to cysteine. However, in contrast to SHNH-DNA, no evidence for serum protein binding of the labeled $MAG_3$-DNA was observed. Since binding to proteins in serum and in tissue as a major disadvantage to the use of oligonucleotides labeled with technetium-99m via the chelator SHNH, the $MAG_3$ chelator is a more useful method of radiolabeling these biomolecules.

In Example 1, we teach acetyl-$MAG_3$ synthesis by reacting triglycine with SATA for 15 min at room temperature. The composition NHS-acetyl-$MAG_3$ is then prepared without a purification step from the first reaction by DCC-mediated coupling to $MAG_3$ of the in situ-generated N-hydroxysuccinimide, which is taught in Example 2. Example 3 teaches how the NHS-acetyl-$MAG_3$, purified only by centrifugation, is coupled in 15 min at room temperature to a 22-base single-stranded DNA through an amine on the 3' end. In Example 4, radiolabeling by transchelation from technetium-99m-tartrate is taught, and in this example, a yield of 84+6% from 5 different experiments and specific activity of 70 microCuries per microgram is obtained within 15 min at room temperature. Throughout these examples, all solutions were sterilized by terminal filtration through a 0.22 micrometer filter (Gelman, Ann Arbor, Mich.), and sterile pipette tips (Brinkmann, Westbury, Mass.) were used. All tubes, etc. were autoclaved prior to use.

EXAMPLE 1
Synthesis of Acetyl-$MAG_3$

As shown schematically in FIG. 1, acetyl-$MAG_3$ was synthesized by reacting triglycine with S-acetylthioglycolic acid N-hydroxysuccinimide ester (SATA) for 15 min at room temperature. S-acetylthioglycolic acid N-hydroxysuccinimide ester (SATA) was obtained from Sigma Chemical Co., St. Louis, Mo. and was used without further purification. To 0.97 milliliters of a 0.225M NaOH was added 50 milligrams of triglycine (264 micromol) and 10 microliters of a freshly-prepared 50 mM EDTA. This solution was passed through a 0.2 micrometer filter to remove amine-containing particulates. A solution of 90 milligrams (390 micromol) of SATA in 340 microl of DMF (dried over molecular sieve) was prepared and was added dropwise to the stirred triglycine solution. After 15 min of stirring at room temperature, the non-aqueous solution was adjusted from an apparent pH of 8.9. to an apparent pH of approximately 2.7 (measured with a glass electrode-pH meter) by the addition of 37.6 microliters of 6M HCl. An initial pH of about 8.9 was selected to deprotonate the amine on triglycine (pK 7.9) but without reaching extreme basic pH values in which the acetyl group on SATA may hydrolyze. The pH was lowered as soon as possible to minimize hydrolysis of the acetyl group. NMR and melting point determinations for the products of this reaction are described below with the products for the second reaction, in Example 2.

EXAMPLE 2
Synthesis of NHS Acetyl-$MAG_3$

Without purification, NHS-$MAG_3$ is Prepared directly from the reaction of Example 1, usually in 15 hrs but in as little as 1–2 hrs by dicyclohexylcarbodiimide (DCC)-mediated coupling to acetyl-$MAG_3$ of the in situ-generated N-hydroxysuccinimide. Dicyclohexylcarbodiimide (DCC) is obtained from from Sigma Chemical Co. (St. Louis, Mo.) and used without further purification. A solution of 60 milligrams (290 micromol) of DCC in 3.6 milliliters of dry DMF is added rapidly to the stirred triglycine/SATA solution (apparent pH of about 5.0). The solution becomes cloudy within 2 min as dicyclohexylurea precipitates. The reaction is stirred at room temperature in the dark for 2–4 hrs and is then cooled to −20° C. for an additional hour for maximum precipitation. After centrifugation at 4° C., 2500 g for 15 min., the clear supernatant is removed.

Due to the presence of water in the DMF solution, the NHS-acetyl-$MAG_3$ preparation in this form is used within 24 hrs of preparation. For long-term storage, the NHS-acetyl-$MAG_3$ water/DMF solution is evaporated to near-dryness in 15–30 min on a rotary flash evaporator (Rotavapur-R, Buchi, Switzerland) and then lyophilized to dryness within 1 hr on a lyophilizer (Virtis, Garden N.Y.). After drying in this fashion, the NHS-acetyl-$MAG_3$ can be stored indefinitely at room temperatures in a dessicator When using the dry, powdered NHS-acetyl-$MAG_3$ for conjugation, an arbitrary value of 50% by weight was assumed for its purity.

The results of the reactions in Examples 1 and 2 were assessed by NMR analysis and melting point determinations. For these analyses, the $MAG_3$ carboxylate intermediate and the NHS-acetyl-$MAG_3$ were each purified on an open column silica gel column (Silica Gel 60, 0.2–0.5 mm particle size, EM Science, Gibbstown N.J.) using acetonitrile as eluant. The NMR analyses were performed in fully deuterated DMSO on a 300 MHz instrument (Varian Unity-300, Varian Associates Inc., San Fernando, Calif.). The chemical shifts for S-acetyl $MAG_3$ were 2.36 (s,3H), $SCOCH_3$; 3.66 (s,2H), $COCH_2S$; 3.72–3.78 (m, 6H), $NCH_2CO$); 8.15–8.36 (m,3H), NHCO. The chemical shifts for NHS-acetyl-$MAG_3$ were 2.38 (s,3H), $SCOCH_3$; 2.80 (s,4H), succinimidyl; 3.68(s,2H), $COCH_2S$; 3.70–3.80 (m, 6H), $NCH_2CO$); 8.20–8.38 (m,3H), NHCO.

The uncorrected melting points were determined (Mel-Temp, Laboratory Devices, Cambridge, Mass.) to be 210–212° C. (dec.) for acetyl-protected $MAG_3$ and 148–151° C. for NHS-acetyl-$MAG_3$. These data demonstrate the chemical properties of the synthesis products.

EXAMPLE 3
DNA Conjugation with $MAG_3$ and SHNH

Two 22-base single-stranded DNA oligonucleotides were purchased (Operon Technologies, Alameda, Calif.) for this investigation. Aliquots of 20–1000 ug of DNA were added to sterile plastic vials which were immediately frozen at −20° C. for storage. Reagent-grade avidin (Molecular Probes, Eugene, Oreg.), disodium ethylenetriaminetetraacetic acid (EDTA) (Aldrich Chemical Co., Milwaukee, Wis.), D-biotin, dicyclohexylcarbodiimide (DCC), L-cysteine, dimethylformamide (DMF), sodium glucoheptonate, sodium tartrate, tricine, triglycine, streptavidin was obtained from Sigma Chemical Co., St. Louis, Mo., and was used without further purification. The base sequences were 5'-biotin-TA ATA CGA CTC ACT ATA GGG AG-amine-3' and its complement, as described previously (Hnatowich D. J., Winnard P. Jr., Virzi F, Fogarasi M, Sano T, Smith C L, Cantor C R, Rusckowski M, *J. Nucl Med* 36: 2306–2314, 1995). A biotin moiety was attached via a 15-member amide-polyether linker to the terminal phosphate on the 5' end while a primary amine was attached to the terminal 3' phosphate group via a 6-member methylene carbon spacer. The molecular mass was about 8 kDa. The melting temperature in physiological saline was calculated to be 62° C. for double-stranded DNA (Wetmur, J. G., Rev Biochem Mol Biology 26: 227–259; 1991). The DNAs were purchased unpurified and were used without further purification. After coupling, the conjugate could be stored for extended periods since the attached $MAG_3$ group was still protected For conjugation with $MAG_3$, a solution of single-stranded amine-derivatized DNA (100–1000 microgram) was prepared at a concentration of 2 milligrams/milliliters in 0.25M $NaHCO_3$-1M NaCl-1 mM EDTA, pH 8.5. The DNA solution was heated to 60–70° C. for 5–10 min to dissociate any DNA duplexes and immediately plunged into ice water. The DMF/water solution of NHS-acetyl-$MAG_3$ was then added to the stirred DNA solution to a $MAG_3$: DNA molar ratio estimated to be 20:1. This solution was incubated at room temperature for 15 min in the dark. The conjugation of the same oligonucleotides with SHNH was achieved by reacting the NHS derivative of SHNH with the DNA primary amine as has been previously described (Hnatowich D. J., Winnard P. Jr., Virzi F, Fogarasi M, Sano T, Smith C L, Cantor C R, Rusckowski M., *J. Nucl Med* 36:2306–2314, 1995) and was similar to that described above for $MAG_3$ conjugation. The DMF solution of NHS-SHNH was added, while vortexing, to the DNA solution until a final molar ratio of SHNH:DNA of 25:1 was reached. The solution was incubated at room temperature in the dark for 1 hr.

For both methods, the conjugated DNAs were purified on a 0.7×20 cm P4 column (BioRad, Melville, N.Y.) eluted with 0.25M $NH_4$Acetate-0.25 mM DTPA. pH 5.2 buffer. The DTPA was added to help prevent radiocolloid formation during radiolabeling. Fractions (0.4 milliliters) off the P4 column were collected and the absorbency (260 nm) of each measured (Hitachi Instruments, Danbury, Conn.). Oligonucleotide concentrations were estimated using an extinction coefficient at 260 nm determined in this laboratory of 30 microliters/micrograms for a 0.1% solution. The absorbency of SHNH and $MAG_3$ under these conditions was found to be negligible. After purification, the concentration of DNA in the peak fractions was typically about 1 milligrams/ milliliters for a conjugation of 1000 microgram of DNA. Both modified DNAs were stored at −20° C. for at least three months. These data illustrate yields of chelator-PNA compositions.

EXAMPLE 4
Oligonucleotide Labeling with Technetium 99m

Preliminary labeling studies comparing tricine, glucoheptonate and tartrate as transchelator were performed at 22–100° C. and at pH values between 5.5–7.6. Since superior labeling efficiencies were consistently achieved with tartrate at room temperature, pH 7.6, the $MAG_3$-conjugated oligonucleotides were eventually radiolabeled with technetium-99m by transchelation exclusively from labeled tartrate (Fritzberg A. R., Nuklearmedzin 1987; 26: 7–12). The technetium-99m-pertechnetate was obtained from a $^{99}$Mo-technetium-99m radionuclide generator (Dupont, Billerica, Mass.). Succinimidyl 6-hydrazinonicotinate-SHNH was obtained from Dr. M. Abrams (Johnson Matthey Inc., West Chester, Pa.).

A fresh 50 milligrams/milliliters solution of sodium tartrate was prepared in sterile 0.5M $NaHCO_3$, 0.25M $NH_4$Acetate, 0.18M $NH_4OH$, pH 9.2. The high pH of the tartrate solution was necessary so that the final pH would be approximately 7.6. In addition, a 1.0 milligrams/milliliters solution of $SnCl_2.2H_2O$ in 10 milliM HCl was prepared just prior to use.

To a sterile test tube containing the acetyl-$MAG_3$-DNA (about 10–100 micrograms, 10–100 microliters) was added sufficient technetium-99m-pertechnetate solution (2–10 microliters) to provide about 100 uCi/ug of DNA. To this was added the tartrate solution to a final concentration of about 6–7 ug/microliters. The stannous ion solution was added immediately thereafter and such that 1 microgram of $SnCl_2.2H_2O$ was added for each 10 $\mu$g of DNA. Higher activities of technetium-99m required proportionately larger volumes of the tin solution.

After 15 min at room temperature, the labeled DNA was purified on a 0.7×20 cm gel filtration column of Sephadex G-25 using sterile 0.25M $NH_4$Acetate, pH 5.2, or saline, as eluant. Radioactivity and absorbency at 260 nm were used to identify and quantitate peak fractions. Preparations were routinely analyzed by size exclusion HPLC using a single 1×30 cm Superdex 200 column (Pharmacia, Piscataway, N.J.). The recovery was routinely recorded. Control labeling was performed in which the native, unconjugated DNA was subjected to the identical labeling procedure to assess the extent of nonspecific labeling.

The SHNH-conjugated oligonucleotides were radiolabeled with technetium-99m by transchelation from tricine as previously described (Hnatowich D. J., Winnard P. Jr., Virzi F, Fogarasi M, Sano T, Smith C L, Cantor C R, Rusckowski M., *J. Nucl Med*, 36: 2306–2314, 1995; Hnatowich D. J., Mardirossian G., Fogarasi M. Sano T, Smith C L, Cantor C R, Rusckowski M, Winnard P. Jr., J. Pharmacol. Exp Ther 276:326–334, 1996). Briefly, a solution of tricine was prepared at neutral pH to which was added a fresh solution of $SnCl_2$. The technetium-99m-pertechnetate solution was then added to the DNA-tin solution and, immediately, a 20-microliters aliquot of the tin-tricine solution was added. After 10 min at room temperature, the labeled DNA was purified on a 0.7×20 cm gel filtration column of Sephadex G-50 using sterile 0.15M saline as eluant. The radiochemical purity was determined by HPLC as described above for the labeling of $MAG_3$-DNA.

The technetium-99m labeled $MAG_3$-DNA was evaluated for stability in comparison to the same DNA radiolabeled with technetium-99m via the hydrazino nicotinamide (SHNH) chelator. The radiolabel is similarly stable to transchelation to cysteine. However, in contrast to SHNH-DNA, no evidence for serum protein binding of the labeled $MAG_3$-DNA is observed.

Optimum labeling conditions were consistently obtained with tartrate as transchelator. Under the set of conditions described above, labeling efficiencies of 84% (s.d. 6%, five separate experiments) were achieved within 15 min at room temperature. Neither raising the temperature or increasing the labeling time greatly improved the labeling efficiency. Specific activities of up to 70 microCuries/microgram were obtained. Control labeling of unmodified DNA under these conditions showed about 0–2% binding.

DNAs which had been coupled with $MAG_3$ have been radiolabeled without loss of efficiency after more than six months of storage at −20° C. These data illustrate that high labeling efficincies of $MAG_3$-PNA can be achieved using mild conditions. That the conjugated DNA could be successfully radiolabeled after storage at refrigerator temperatures for more than 6 months strongly suggests that the sulfuir was still protected and that the deprotecting group is hydolyzed away during labeling, possibly by the excess stannous ion present to reduce the technetium-99m-pertechnetate.

EXAMPLE 5
HPLC Studies

In addition to measuring radiochemical purity, size exclusion HPLC analysis was also used to establish whether the conjugation and labeling procedure had diminished the ability of the labeled DNA to bind to avidin through the biotin moiety of the DNA and to hybridize with its complementary single-stranded DNA. The radiolabeled $MAG_3$-DNA was analyzed by HPLC before and after the addition of avidin and before and after the addition of the complementary DNA bound to avidin (in which all unoccupied biotin sites were saturated with D-biotin).

To test the ability of the labeled DNA to bind to avidin through its biotin moiety, a four-fold molar excess of avidin was added to a solution of labeled DNA. After 1 hr., the solution was reanalyzed by HPLC. As a control, the identical analysis was also performed after the addition of biotin-saturated avidin to the labeled DNA.

To test the ability of the labeled DNA to hybridize to its complement, the complementary unlabeled DNA-avidin construct was first prepared by adding the complementary DNA at a four-fold molar excess to avidin and allowing 1 hr at room temperature for the binding of DNA through its biotin moiety. The remaining biotin-binding sites were then blocked by the addition of a 10-fold molar excess of D-biotin. The preparation was purified over a 0.7×20 cm column of Sephadex G75 using sterile 0.25M $NH_4$Acetate-0.5M NaCl pH 7.2 buffer as eluant.

Hybridization was accomplished by incubating 0.4 microgram of the labeled DNA in saline with a 4-fold molar excess of the complementary DNA-avidin preparation. After 1 hr at room temperature, the unpurified solution was analyzed by HPLC. The identical study was performed with the biotin-saturated complementary DNA-avidin preparation.

Size exclusion HPLC radiochromatograms were obtained on a single 1×30 cm Superdex 200 column (Pharmacia, Piscataway, N.J.) and 0.1M sodium phosphate, pH 7 eluant.

FIG. 2 presents several radiochromatograms obtained by size exclusion HPLC analysis. Panel A is that of the radiolabeled DNA itself. Panel B is the result of adding the labeled DNA to biotin saturated avidin. In this case, the absence of a shift to higher molecular weight suggests the absence of nonspecific binding of the labeled DNA to avidin. Panel C is the result of adding the labeled DNA to unsaturated avidin. In this case, the pronounced shift in radioactivity to higher molecular weight is the result of binding of the DNA to avidin through its biotin moieties. The shift indicates that the radiolabel is on the DNA as expected and that the conjugation and labeling procedures did not affect the biotin moiety in its affinity for avidin. The partial shift is most likely explained by assuming that approximately half the DNA molecules were obtained without the biotin group attached.

Lastly, Panel D shows the result of adding the labeled DNA to avidin to which the complementary DNA had previously been bound through its biotin moiety. In this case, the shift is quantitative, confirming that the radiolabel is on the DNA and that the conjugation and labeling procedures did not affect the ability of the DNA to hybridize under the conditions of this measurement.

EXAMPLE 6

Cysteine Challenge

The stability of technetium-99m-$MAG_3$-DNA to cysteine transchelation compared to that of technetium-99m-SHNH-DNA was evaluated at one cysteine concentration and after 1 hr in 37° C. 25 milliM $Nll_4$Acetate, pH 7.0 buffer. Both labeled DNAs were added at a final concentration of 0.4 mM to a solution of 1-cysteine in 25 mM $NH_4$Acetate, pH 7.0 such that the cysteine: DNA molar ratio was 650:1 (Hnatowich D J, Virzi F, Fogarasi M, Winnard P. Jr., Rusckowski M, Nucl Med. Biol 1994; 21: 1035–1044). After an incubation period of 1 hr in a 37° C. water bath, samples were removed for size exclusion HPLC analysis. The area under the DNA and cysteine peaks in the radiochromatographic profiles were evaluated and compared between the two labeling methods.

Figure 3A:
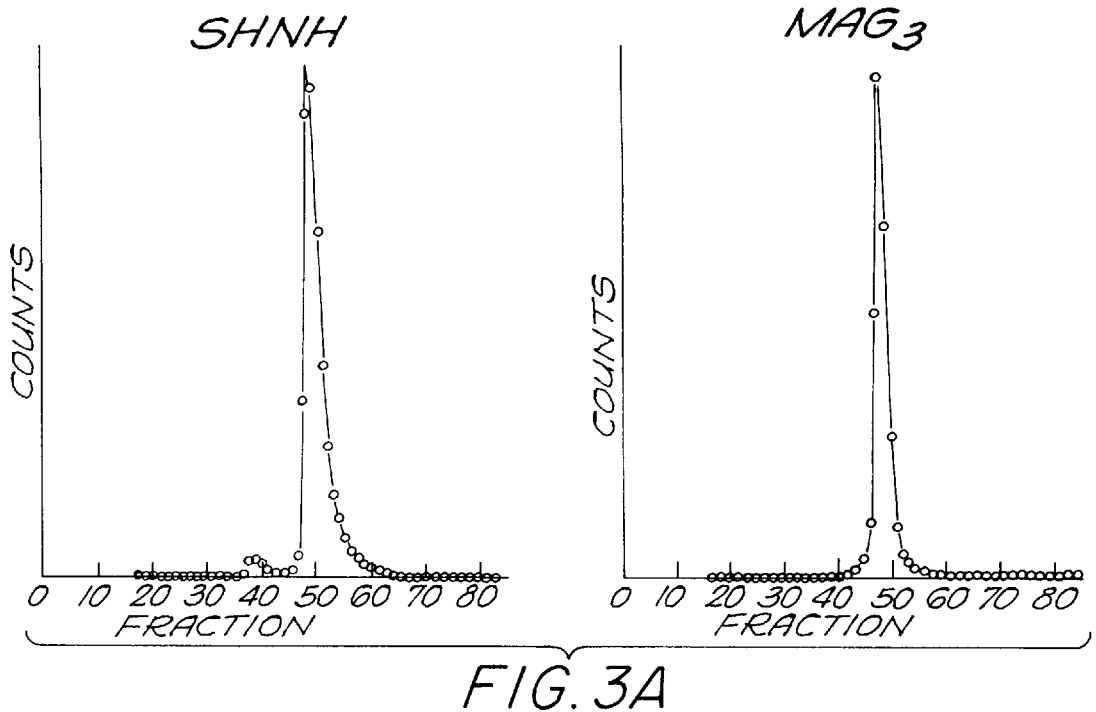
FIG. 3 shows radiochromatograms obtained by size exclusion HPLC analysis of SHNH-coupled DNA (left column) and MAG$_3$-coupled DNA (right panel) after labeling with $^{99m}$Tc. Panel A: of the labeled DNAs themselves; Panel B: following incubation of the labeled DNAs in solution with a 650-fold molar excess of cysteine; Panel C: after 1 hr. of incubation in 37° C. serum.
Figure 3B:
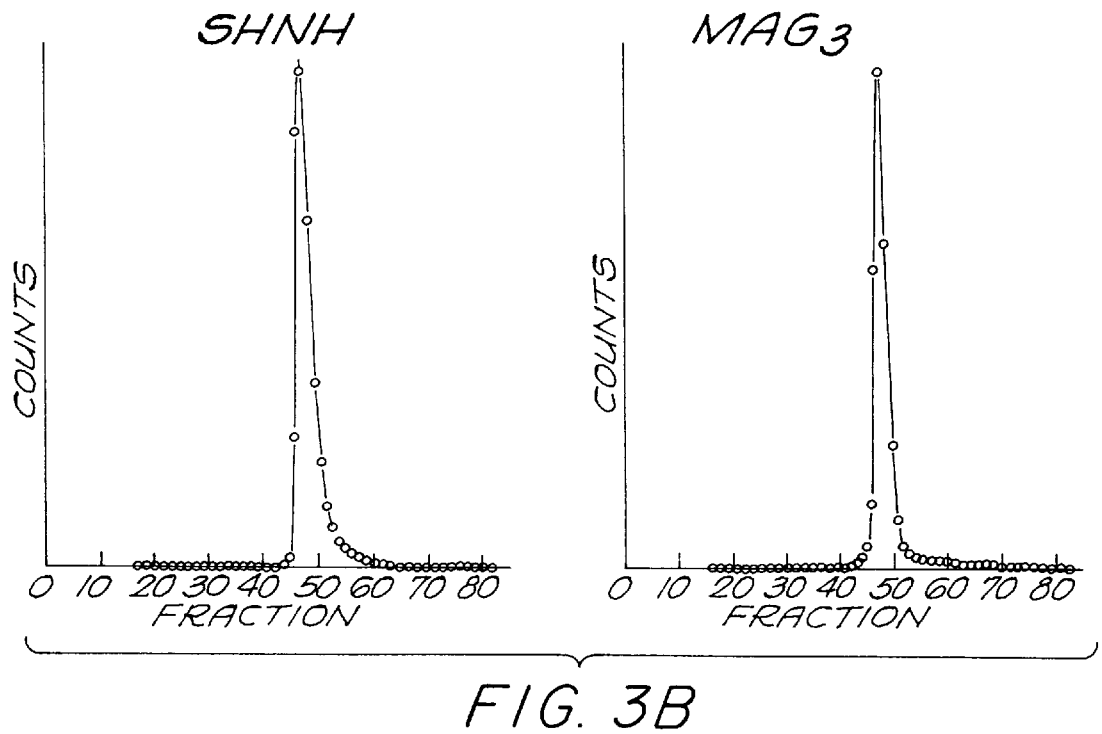
Figure 3C:
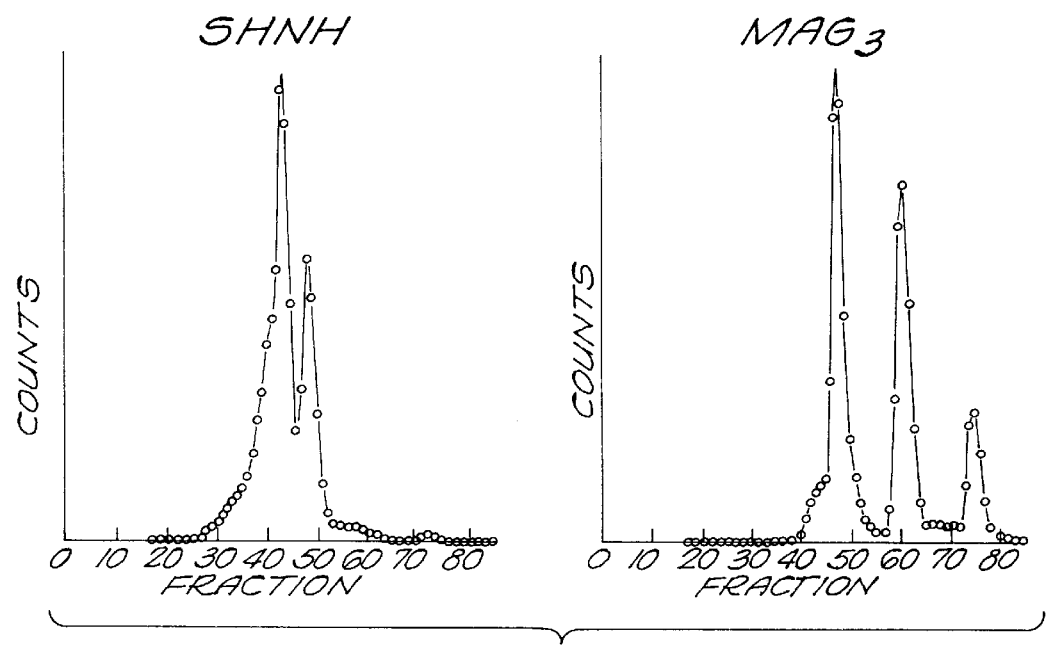
Figure 4A:
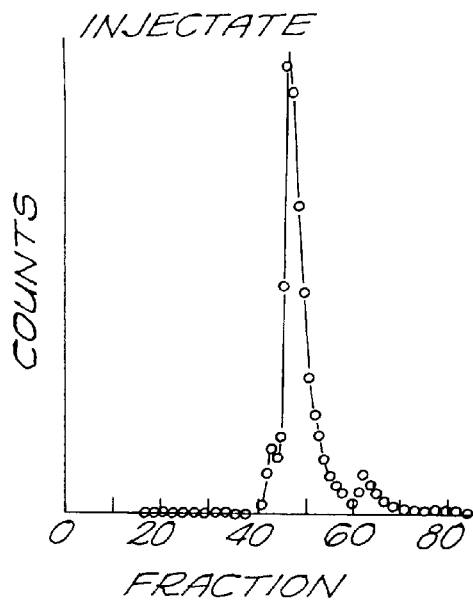
FIG. 4 shows radiochromatograms obtained by size exclusion HPLC analysis of $^{99m}$Tc-MAG$_3$-DNA itself (top row) and after 10 min. to 24 hr. in 37° C. serum.
Figure 4B:
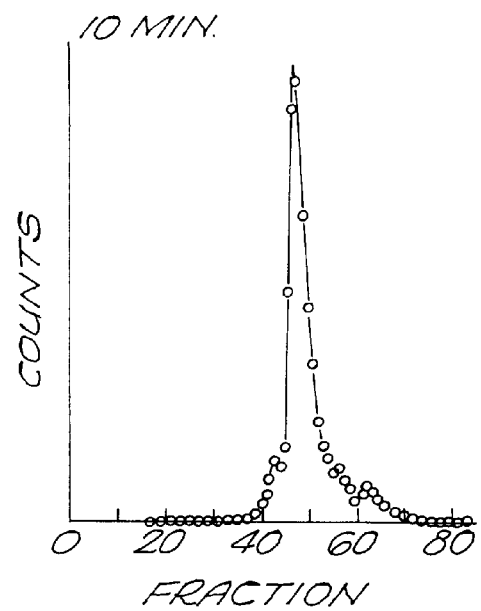
Figure 4C:
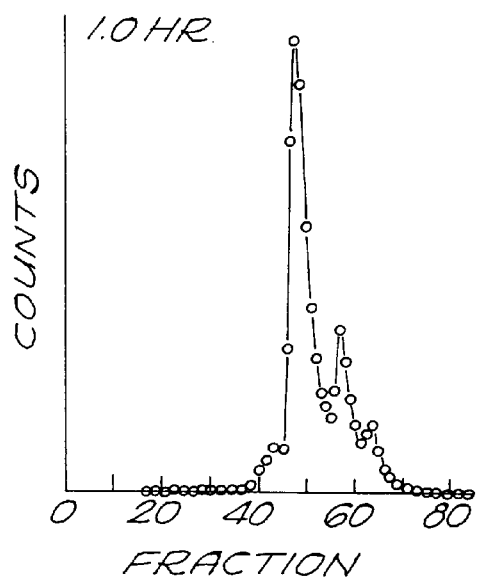
Figure 4D:
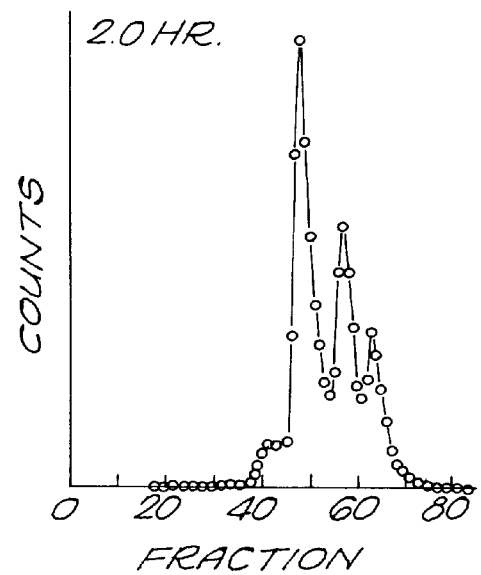
Figure 4E:
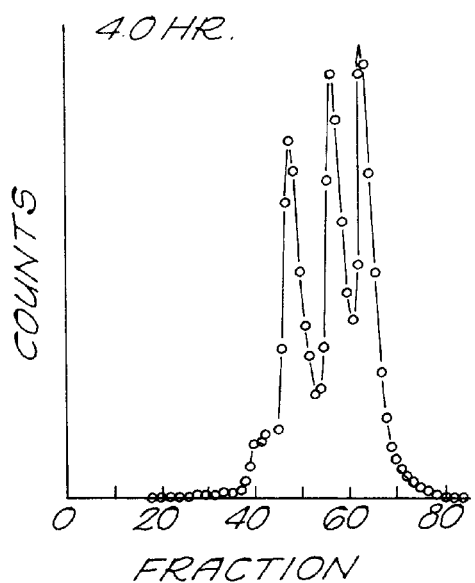
Figure 4F:
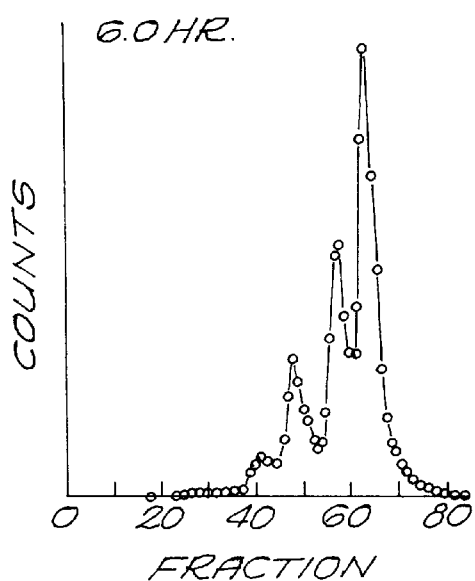
Figure 4G:
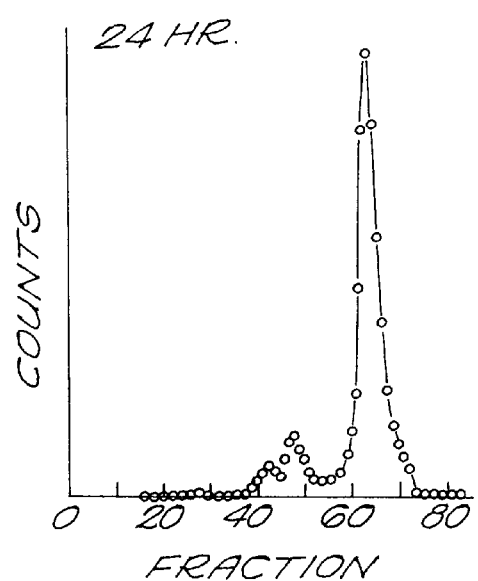

FIG. 3 presents radiochromatograms obtained by size exclusion HPLC analysis of the same single-stranded phosphodiester DNA labeled with technetium-99m via both SHNH and $MAG_3$. In the case of both labeling methods, panel A presents the radiochromatograms of the radiolabeled DNAs themselves. Panel B is the result of incubating the radiolabeled DNAs at 37° C. with cysteine at a 650 molar excess for 1 hr. Under the conditions of this analysis, radiolabeled cysteine appears as a peak in fraction 75 (Hnatowich D J, Virzi F, Fogarasi M, Winnard P. Jr., Rusckowski M., Nucl Med. Biol 1994; 21: 1035–1044). A small peak may be present in the radiochromatogram of $MAG_3$; nevertheless the stability of both the SHNH and $MAG_3$ chelates towards transchelation to cysteine is apparent. This indicates that the radionuclide-chelator complexes with each of the chelators are stable.

EXAMPLE 7

Serum Incubation Studies

Labeled $MAG_3$-DNA was incubated at a concentration of 10 micrograms/milliliters in fresh human serum at 37° C. Samples were periodically removed over 24 hrs for size exclusion HPLC analysis.

The last panel (C) in FIG. 3 shows the result of analyzing serum samples into which the labeled DNA were added. In the case of the SHNH chelator after 1 hr of incubation at 37° C., the technetium-99m radiolabel is primarily on serum proteins as shown by the shift to higher molecular weight (earlier fractions). This property has been observed previously for DNAs radiolabeled with technetium-99m via the SHNH chelator (Hnatowich D. J., Winnard P. Jr., Virzi F, Fogarasi M, Sano T, Smith C L, Cantor C R, Rusckowski M., J Nucl Med 36: 2306–2314, 1995; Hnatowich D. J., Mardirossian G., Fogarasi M. Sano T, Smith C L, Cantor C R, Rusckowski M, Winnard P. Jr., J. Pharmacol. Exp Ther 276: 326–334, 1996). In the $MAG_3$ case, by contrast, in the $MAG_3$ case, very little serum protein binding is evident. In its stead, several lower molecular weight peaks are present and are likely due to nuclease digestion of the single-stranded phosphodiester DNA. Similar low molecular weight catabolites have been observed previously in the case of DNA radiolabeled with $^{111}$In under conditions which also minimized serum protein binding (Hnatowich D. J., Winnard P. Jr., Virzi F, Fogarasi M, Sano T, Smith C L, Cantor C R, Rusckowski M, J. Nucl Med 36: 2306–2314 1995).

The properties of technetium-99m labeled $MAG_3$-DNA in 37° C. serum over 24 hrs are shown in FIG. 4. After 24 hrs of incubation, very little intact labeled DNA remains with the activity present primarily the lowest molecular weight catabolite peak as seen in previous results.

Experience with the SHNH chelator for antibody labeling (Abrams M. J., Juweid M., tenKate C. I., Schwartz D. A., Hauser M. M., Gaul F. E., Fuccello A. J., Rubin R. H., Strauss H. W., Fischman A. J., J. Nucl Med 31: 2022–2028, 1990.; Hnatowich D. J., Mardirossian G., Ruscowski M., Fogarasi M, Virzi F, Winnard P. Jr., J. Nucl Med 34; 109–119, 1993) has shown that technetium-99m can be attached effectively and stably in this manner. However, high molecular weight aggregates have been observed and have been attributed to peculiarities of the technetium-99m-SHNH chelate (Hnatowich D. J., Mardirossian G., Ruscowski M., Fogarasi M, Virzi F, Winnard P Jr., J. Nucl Med 34; 109–119, 1993). Whereas this property may not interfere seriously in the case of high molecular weight species such as protein, it may become more serious when peptides and smaller molecules are labeled. That the same single-stranded DNA displays minimal tendency to bind nonspecifically to serum proteins when labeled with $^{111}$In via a DTPA chelate, but is strongly bound to protein when labeled with technetium-99m via SHNH (Hnatowich D. J., Winnard P. Jr., Virzi F, Fogarasi M, Sano T, Smith C L, Cantor C R, Rusckowski M, J. Nucl Med 36: 2306–2314, 1995). This property influences the biodistribution of technetium-99m when administered to mice on a SHNH-derivatized DNA, (Hnatowich D. J., Mardirossian G., Fogarasi M. Sano T, Smith C L, Cantor C R, Rusckowski M, Winnard P. Jr., J. Pharmacol. Exp Ther 276: 326–334 1996).

For consideration of alternative chelators to SHNH for the labeling of oligonucleotides with technetium-99m, the imidosuccinimide $MAG_3$ S-acetyl tripeptide chelator is compared in these Examples. This chelator binds technetium-99m for kidney function investigations (Fritzberg A R., Kasina S., Eshima D., Johnson D. L, J. Nucl Med 27: 111–116; 1986) and when conjugated to proteins such as antibodies, (Fritzberg A. R., Berninger R. W., Hadley S. W. et al., Pharmaceutical Res. 5: 325–334; 1988. Bioconjugate Chem 1: 431–437; 1990). No evidence of nonspecific protein binding through this chelate has been reported.

The prior use of this chelator involved protection with a benzoyl group, which requires temperatures of 100° C. for hydrolysis (Fritzberg A. R., Berninger R. W., Hadley S. W. et al., Pharmaceutical Res. 5: 325–334; 1988, Bioconjugate Chem 1: 431–437; 1990; Goldrosen M H., Biddle W C., Pancook S. Bakshi S., Vanderheyden J-L., Fritzberg A. R., Morgan A. C., Foon K. A., Cancer Res. 50: 7973–7978; 1990) and is a disadvantage in its use to radiolabel temperature-sensitive molecules. Investigators have resorted to pre-conjugation labeling in these cases.

The use of an acetyl group for protection can improve the $MAG_3$ labeling method both by simplifying both the synthesis and deprotection/labeling. The ideal protecting group will be stable to indefinite storage of the conjugated molecule and would hydrolyze under mild conditions only at the point of labeling with technetium-99m. The acetyl group appears to satisfy these requirements. Firstly, the acetyl protected imidosuccinimde-$MAG_3$ may be prepared in a one-pot, two-step synthesis not requiring intermediate purification steps. Conjugation to an amine-derivatized single-stranded DNA is successful.

To prevent artifacts due to potential hydrogen bonding, accordingly, the pH of the buffer used to purify and store the radiolabeled DNA was reduced from 7.0 to 5.2 with the result that this peak no longer appeared.

Labeling efficiencies were similar for tartrate-transchelated $MAG_3$-conjugated DNA relative to that achievable with SFINH-conjugated DNA. In the latter case, 70% labeling efficiency was routinely observed when using tricine as transchelator and specific activities in excess of 100 microCuries/microgram have been obtained (Hnatowich D. J., Winnard P. Jr., Virzi F, Fogarasi M, Sano T, Smith C L, Cantor C R, Rusckowski M., J. Nucl Med 36: 2306–2314, 1995). Labeling efficiencies with $MAG_3$-DNA averaged about 85% with specific activities of about 70 microCuries/micrograms. These values did not increase at 100° C.

In this investigation, an important observation is the different extents to which labeled DNAs to bind to serum proteins. Whereas the technetium-99m label was rapidly bound nonspecifically to serum proteins in 37° C. serum when incubated as labeled SHNH-DNA, no evidence of serum protein binding was apparent even after 24 hrs in this medium as labeled $MAG_3$-DNA (FIG. 4). Rather, low molecular weight peaks were evident in the HPLC radiochromatograms and are almost certainly due to nuclease digestion in serum of the phosphodiester DNAs. In an earlier investigation, we observed similar low molecular weight peaks following serum incubation in the case of a $^{111}$In-labeled DNA which, unlike technetium-99m-SHNH-DNA, showed no evidence of nonspecific binding to serum proteins and therefore no protection against nucleases (Hnatowich D. J., Winnard P. Jr., Virzi F, Fogarasi M, Sano T, Smith C L, Cantor C R, Rusckowski M., J. Nucl Med 36: 2306–2314, 1995).

It appears that from the Examples above $MAG_3$ is a useful chelator for DNA since its synthesis has been simplified and the labeling procedures used in this investigation have provided adequate labeling efficiencies and specific activities. Furthermnore, unlike the SHNH chelate, the $MAG_3$ chelate of technetium-99m shows a limited tendency to bind nonspecifically to proteins.

Because of the instability of the naturally-occurring form DNA, this invention now teaches examples with PNA, peptide nucleic acid, in which the phosphodiester sugar-phosphate backbone of DNA has been replaced with a close-up peptide backbone. The following examples illustrate these teachings.

EXAMPLE 8
PNA Labeling

Two complementary 15-base single-stranded PNAs were synthesized by PerSeptive Biosystems, Framingham, Mass. One strand was derivatized with a primary amine on the amino terminus (i.e. 5' equivalent) end via a 17-member ethylene-ether linkage. The complementary sequence was prepared with a biotin group on this end via the same linker. The base sequences were $NH_2$-$(CH_2)_2O(CH_2)_2$ $OCH_2CONH(CH_2)_2O(CH_2)$ $OCH_2CO$-TGT-ACG-TCA-CAA-CTA-$CONH_2$ and biotin-$(CH_2)_2O(CH_2)_2$ $OCH_2CONH$ $(CH_2)_2O(CH_2)OCH_2CO$-TAG-TTG-TGA-CGT-ACA-$CONH_2$. The melting temperature (i.e., the temperature at which half the base pairs have dissociated) in physiological saline of the duplex was calculated to be 72° C. The calculated molecular masses were 4336 and 4634 Da respectively and were observed by mass spectrometry to be 4340 and 4635 Da. Purity of both chains was established by reverse phase HPLC (in both cases showing a single peak) and mass spectrometery (showing one predominant peak). The PNAs were lyophylized, stored dry and dissolved when needed in sterile water to a concentration of 4 milligrams/milliliters. After solubilization, aliquots of 20–1000 micrograms of PNA were added to plastic vials which were immediately frozen at −20° C. for storage. Avidin (Sigma Chemical Co., St. Louis, Mo.) was purchased and used without further purification. The technetium-99m-pertechnetate was obtained from a $^{99}$Mo-technetium-99m radionuclide generator (Dupont, Billerica, Mass.). Streptavidin-conjugated magnetic polystyrene beads, 1 micrometer in size (BioMag, PerSeptive Biosystems, Framingham, Mass.), were stored wet at refrigerator temperatures as recommended by the manufacturer. The capacity of the beads for biotin was reported by the manufacturer to be 1.5 nanogram of biotin per milligrams of beads.

The desired volume of the 4 milligrams/milliliters water solution of the amine-derivatized single stranded PNA was made 0.36M $NaHCO_3$, 1.4M NaCl, and 1.4 milliM DTPA, pH 9.3. The NHS-acetyl-$MAG_3$ was dissolved in dry DMF at a concentration of 20 milligrams/milliliters. A volume of the DMF solution representing a molar ratio of $MAG_3$ to PNA of approximately 20:1, was added to the PNA solution during vortexing. The solution (now containing no more than 10% DMF) was incubated at room temperature for 1 hr. The conjugated PNA was purifed over a 0.7×30 cm column of P4 (BioRad, Melville, N.Y.) using 0.25M ammonium acetate, 0.25 mM DTPA, pH 5.2 as eluant. The final PNA concentration was determined by UV absorption at 260 nanometers using an extinction coefficient determined in this laboratory of 33 microliters/micrograms and was usually about 0.3 milligrams/milliliters.

The coupled PNA was usually stored frozen at −20° C. for no more than one week before use. Generally, 150 micrograms of the conjugated PNA was labeled on each occasion. To the PNA solution (about 300 microliters) was added 2.35 milligrams of sodium tartrate (Sigma) from a fresh 50 milligrams/milliliters solution in 0.5M ammonium bicarbonate, 0.25M ammonium acetate, 0.1 8M ammonium hydroxide, pH 9.4 buffer, followed by about 5 milliCuries of technetium-99m-pertechnetate generator eluant (20 microliters). Finally, 17 micrograms of tin(II) chloride (Sigma) from a fresh 1 milligrams/milliliters solution in 10 mM HCl was quickly added with agitation. The labeled PNA was purified on a 0.7×30 cm column of P4 using saline as eluant. The identical labeling procedure was performed on the native, uncoupled PNA as a control.

Each preparation of radiolabeled PNA was analyzed by size exclusion high performance liquid chromatography (HPLC) using a single 30 cm Superose 12 column (Pharmacia, Piscataway N.J.) with both in-line radioactivity and UV detection and 0.05M phosphate, pH 7 eluant. Recovery of radioactivity was routinely determined. Confirmation of labeling was established by HPLC analysis before and after adding the sample to streptavidin-conjugated magnetic beads to which the biotinylated complementary PNA was bound (see below). Loss of radioactivity from solution was due to binding by hybridization of the labeled PNA to the beads.

Figure 5A:
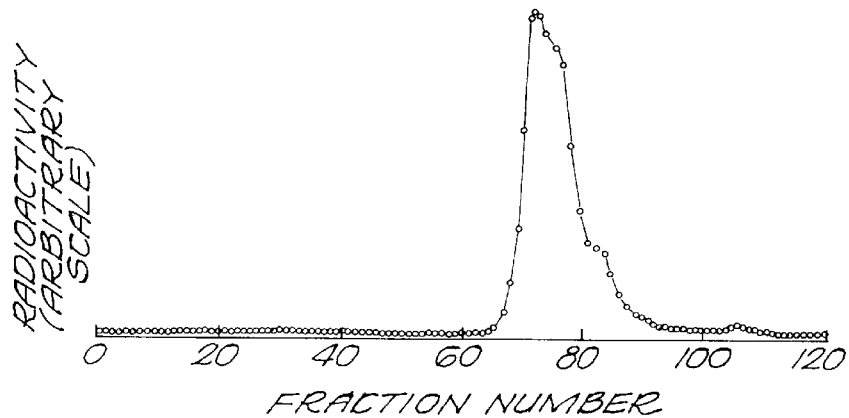
FIG. 5 shows size exclusion HPLC radiochromatograms of labeled PNA in buffer (A), after the addition of biotinylated complementary PNA (B), and after the addition of avidin to the PNA—PNA duplex (C).
Figure 5B:
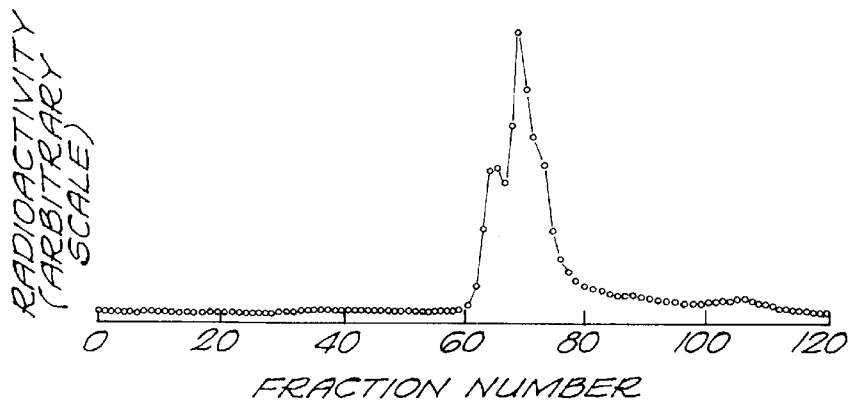
Figure 5C:
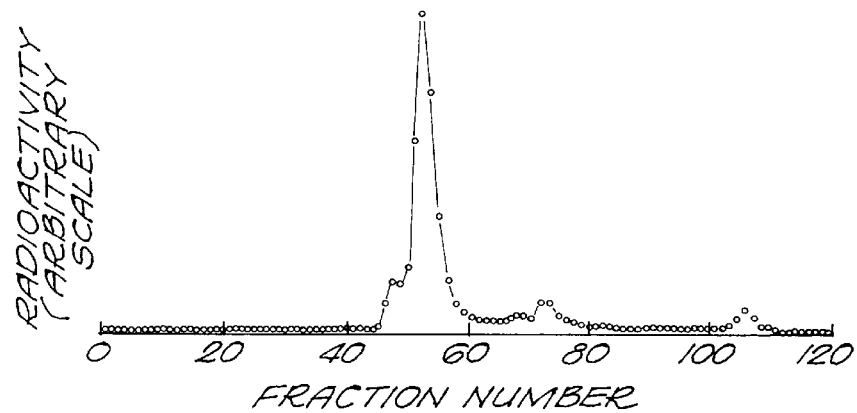

Labeling efficiencies varied from 30–70% and specific activities as high as 100 microCuries/micrograms of PNA were achieved. Control studies in which the unconjugated PNA was labeled showed less than 1% labeling under identical conditions. The HPLC radiochromatographic profile of the labeled and purified PNAs usually consisted of three distinct peaks, the relative intensities of which varied from preparation to preparation. FIG. 5A presents a radiochromatographic profile of one such preparation. That the label was on PNA was confirmed by adding to the labeled PNA solution an excess of complementary PNA. The radiochromatogram resulting from this addition is shown in FIG. 5B and may be compared to the radiochromatogram of the labeled PNA itself (FIG. 5A). A slight shift to higher molecular weight (i.e. earlier fractions on left) has occurred in the case of each peak in the triplet and is the result of PNA—PNA hybridization. Further evidence for labeled PNA is shown in FIG. 5C. In this case, avidin was added to the PNA—PNA duplex to bind the complementary PNA through the biotin moiety. The shift in the radiochromatographic profile is now more pronounced, as expected from the much larger size, and is nearly quantitative. That this shift is not due to nonspecific binding of the label to avidin was established in a repeat study in which avidin was added to the labeled PNA without the prior addition of complementary PNA. These data show that the radiolabeled PNA hybridizes in vitro, and that the biotin moiety functions to bind to streptavidin.

EXAMPLE 9

Rate of Hybridization

Complementary PNA was bound to streptavidin on magnetic beads through its biotin moiety. The suspension of beads was rinsed three times with a washing buffer consisting of 20 mM tris, 2M sodium chloride, 1 mM EDTA, and 0.1% tween 20, adjusted to pH 7.0 and six additional times with a 1:1 dilution in water of this buffer. The beads were manipulated for washing by using a magnetic separator (MPC, Dynal, A. S., Lake Success, N.Y.). Following the last wash, the beads were incubated for 30 min with biotinylated complementary PNA at 6 micrograms of PNA per milligrams of beads (i.e. 100% of saturation) in the washing buffer. The beads were then washed five additional times with the diluted washing buffer.

The rate of hybridization of the labeled PNA to its complement under the conditions of this study was determined at room temperature by adding 1 micrograms of labeled PNA to 300 microliters of complementary PNA attached to beads and suspended at a 1 milligrams/milliliters concentration in 10 mM tris, 1M sodium chloride, 0.5 mM EDTA, 0.05% tween 20, adjusted to pH 7.0 buffer. Samples were removed for analysis periodically over 24 hrs. The beads in each sample were separated magnetically from the solution, washed five times in the washing buffer and counted in a NaI(Tl) well counter. As a control, the identical study was repeated with beads without the complementary PNA.

Figure 6:
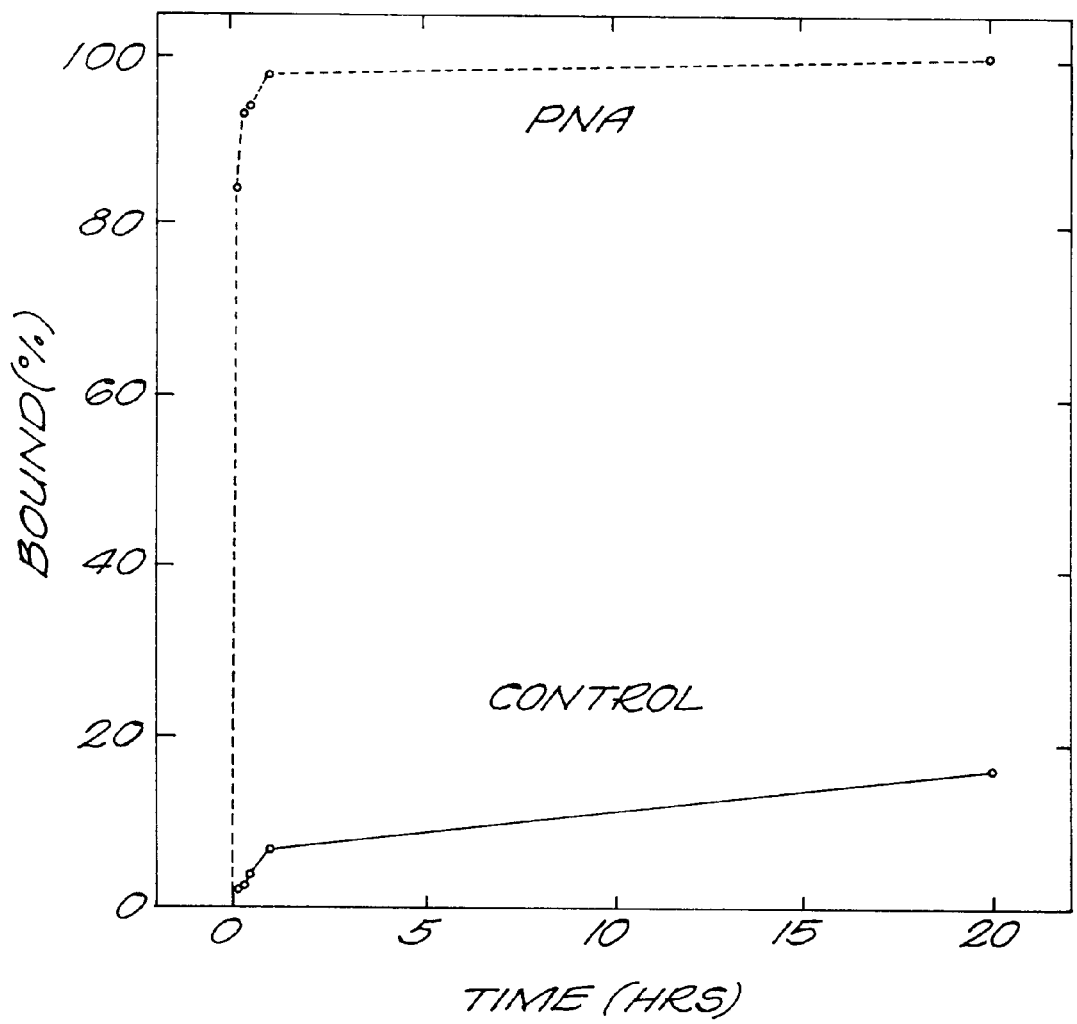
FIG. 6 shows the rate of hybridization of labeled PNA in pH 7 buffer to complementary PNA immobilized on beads. Control refers to identical study using beads without PNA.
Figure 7A:
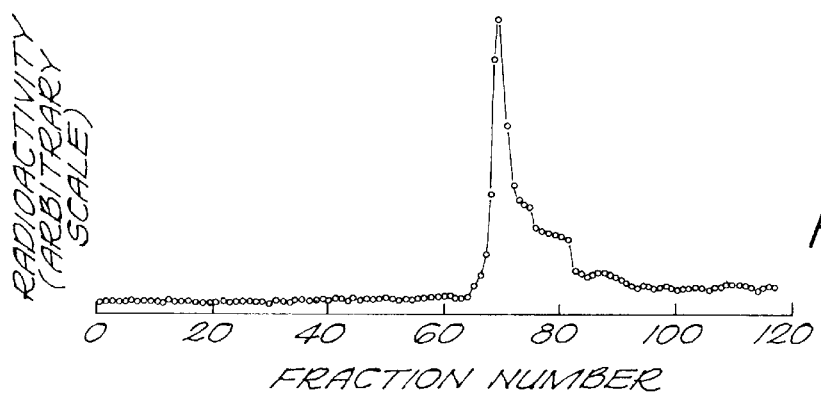
FIG. 7 shows size exclusion HPLC radiochromatograms of labeled PNA in buffer (A), after 1 (B) and 24 hrs (C) of incubation in 37° C. human serum, and after 24 hrs. in saline (D).
Figure 7B:
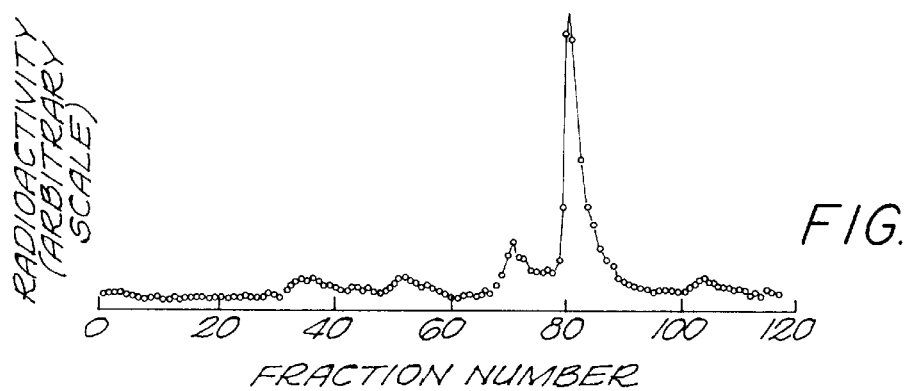
Figure 7C:
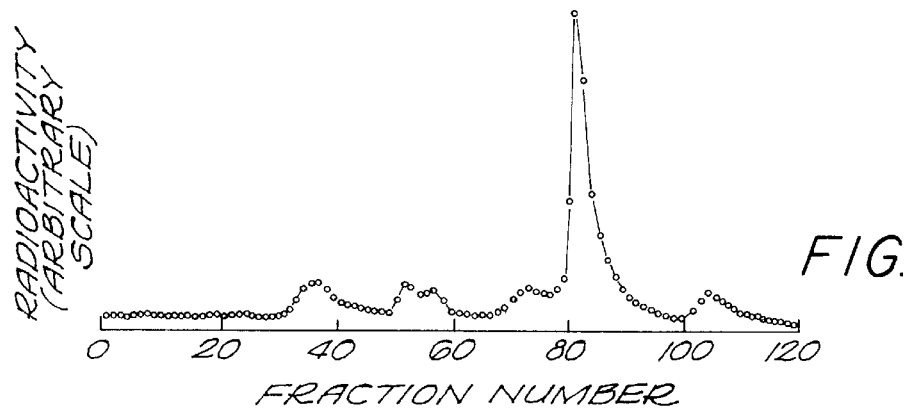
Figure 7D:
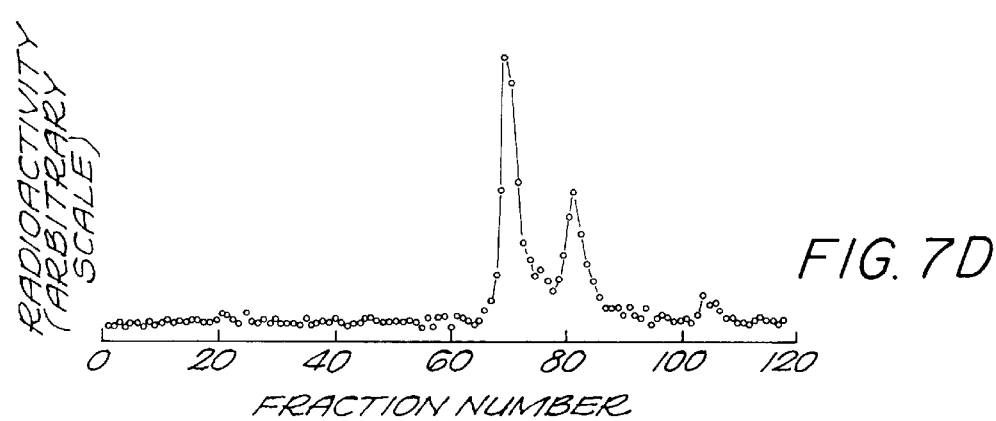
Figure 8A:
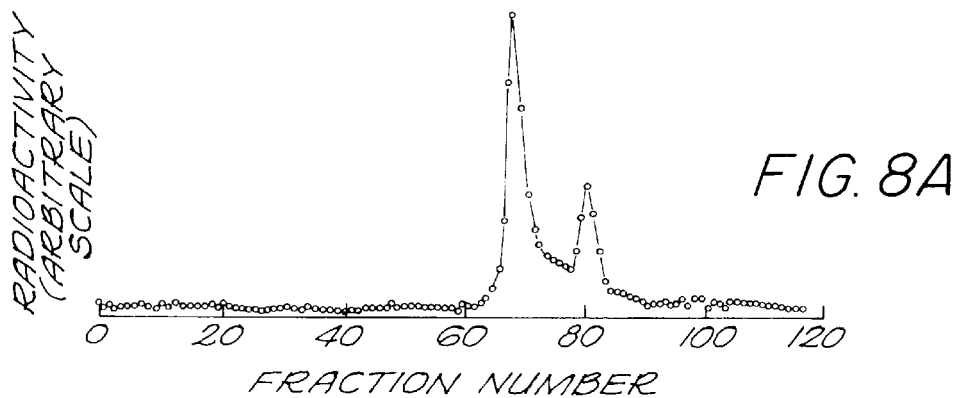
FIG. 8 shows size exclusion HPLC radiochromatograms of labeled PNA in buffer (A), labeled PNA in 37° C. human serum for 1.5 hr. (B), the 1.5 hr. serum sample after removing labeled PNA by adding complementary PNA immobilized on beads (C), and the 1.5 hr. serum sample after adding beads without complementary PNA as control.
Figure 8B:
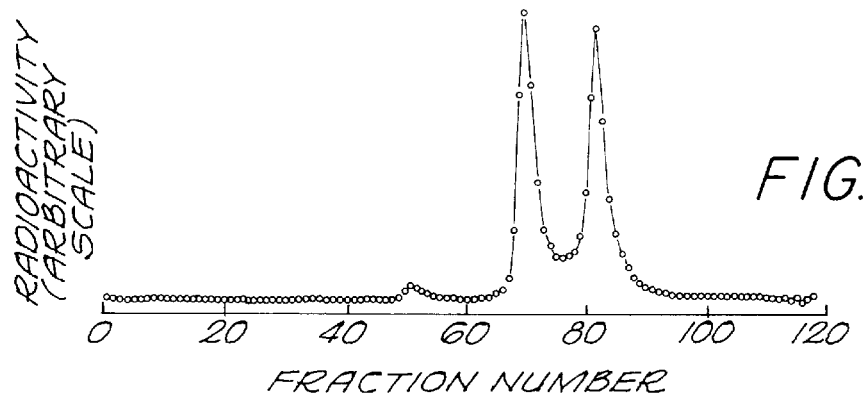
Figure 8C:
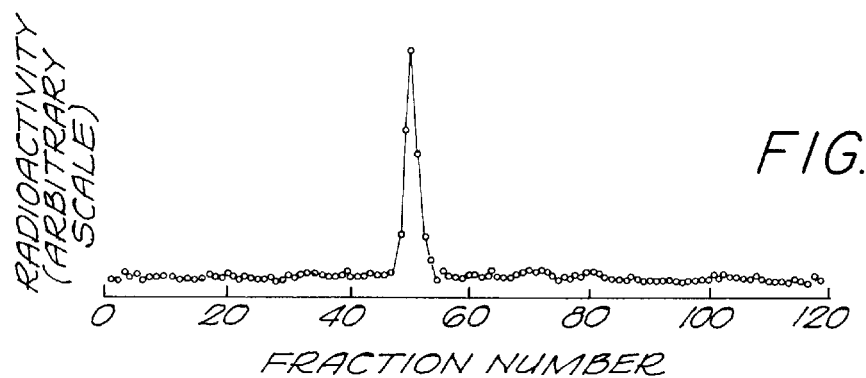
Figure 8D:
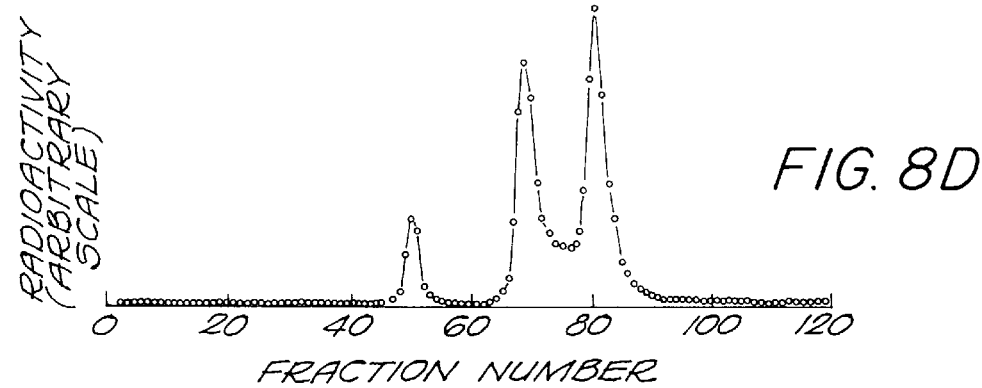

FIG. 6 shows the percentage of labeled PNA bound to complementary PNA on beads as a function of. time with early time points separated by 10 min. Under the conditions of this study, hybridization occurs rapidly and is completed within an hour, and mostly completed within the first 10 minutes. The extent of nonspecific binding of labeled PNA to the beads is minimal, as shown by the control study in which identical beads without PNA were used. These data show that PNA molecules form double-stranded DNA complexes rapidly with complementary strands.

EXAMPLE 10

Serum and Whole Blood Incubations

Labeled PNA was incubated at a concentration of about 5 micrograms/milliliters in fresh 37° C. human serum from two healthy volunteers and in fresh mouse serum. Samples were periodically removed over 24 hrs for HPLC analysis using a 0.1M sodium phosphate, 0.15M saline buffer, pH 7.0 eluant. The identity of labeled PNA peaks in the serum incubate was confirmed by HPLC analysis before and after the addition of 200 micrograms of complementary PNA beads to 100 microliters of the serum.

To evaluate whether the labeled PNA accumulates in formed elements, the labeled PNA was also added to fresh human whole blood with EDTA anticoagulant. The whole blood was incubated at 37° C. with gentle agitation every 15–20 min. Samples were removed at 1 and 24 hrs and separated by centrifugation. The formed elements (material of cellular origin) were washed three times with 0.1M PBS, 0.15M NaCl, pH 7.4, and counted in a NaI(Tl) well counter.

FIG. 7 presents radiochromatographic profiles for labeled PNA after 1 and 24 hrs of incubation in 37° C. human serum and after 24 hrs. in saline. Multiple peaks are again apparent for the labeled PNA in FIG. 7A. In serum, minimal binding of the label to serum proteins is apparent (FIGS. 7B and 7C). The radioactivity ratios among the triplet PNA peaks have been consistently observed to changes in serum in favor of the peak eluting in fraction 83. One peak, eluting in fraction 105 in the figure, is probably the result of catabolism. These general features were also observed during incubations in mouse serum and in human serum. A change in the radioactivity profile also occurs during incubation in room temperature saline (FIG. 7D)

To help identify radioactive peaks in serum due to labeled PNA, complementary PNA bound to streptavidin beads were added to a 1 hr serum sample and the sample reanalyzed after filtration to remove the beads. FIG. 8 shows the radiochromatogram of the labeled PNA initially in saline (FIG. 8A) and after 1.5 hrs in serum before (FIG. 8B) and after (FIG. 8C) extraction of labeled PNA. Only the serum bound radioactivity remains after extraction. As a control against nonspecific binding, the identical serum sample was extracted under identical conditions except with beads without complementary PNA. As shown (FIG. 8D) the radiochromatogram is in this case unchanged.

Under the conditions of incubation of labeled PNA in whole blood described above, radioactivity bound to formed elements was 1.0% and 2.7% at 1 and 24 hrs., respectively. This data indicates that radionuclide-$MAG_3$-PNA is very stable, and that little binds non-specially to serum or permeates material of cellular origin. These data indicate that the radionuclide-$MAG_3$-PNA composition is very stable in serum, that little of the radioactivity binds to serum proteins or is catabolized, and that little is associated with cellular material or cellular debris.

EXAMPLE 11

Homogenate and Urine Analysis Studies

Normal CD-1 male mice (Charles River, Wilmington, Mass.) were injected via the tail vein with 0.1 milliliters of 0.1 5M saline containing about 5–10 micrograms (about 100 microCuries) of labeled PNA, and samples of urine were obtained at 1 hr post administration. The animals were sacrificed by cervical dislocation at 2.5 hrs. and the kidneys removed. Homogenates were prepared in a 15 milliliters tissue grinder (Dounce, Wheaton, Millville, N.J.) in ice-cold 0.2M sodium acetate buffer, pH 5. After grinding, samples were sonicated for 0.5–1 min at 300 watts on ice and then centrifuged at 3500 rpm at 4° C. for 15 min. The pellet and supernatant were counted separately and aliquots of the supernatant were also analyzed by HPLC.

Mouse urine collected 1 hr post administration was analyzed by HPLC before and after adding the complementary PNA beads to establish the extent to which radioactivity in urine was technetium-99m-MAG$_3$-PNA. Control studies consisted of the identical assay in which beads without PNA were added to the urine sample.

Figure 9A:
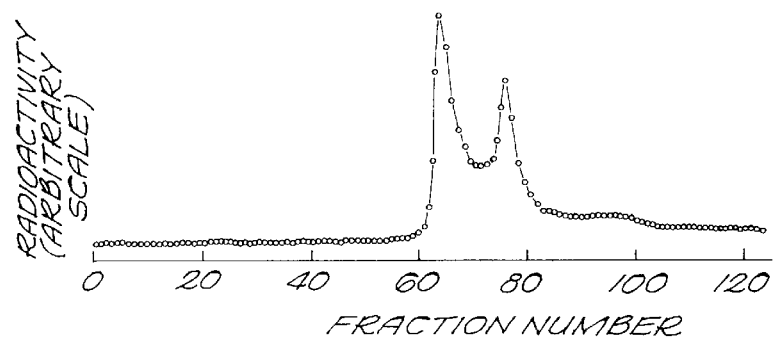
FIG. 9 shows size exclusion HPLC radiochromatograms of labeled PNA in buffer (A) and of several samples obtained at 2.5 hrs. post administration of labeled PNA to a mouse which include a serum sample (B), the soluble fraction of a kidney homogenate (C), urine (D) and the 2.5 hrs. urine sample (B), the 1.5 hr. serum sample after adding complementary PNA immobilized on beads to extract radiolabeled PNA (C) and the 2.5 hrs. urine sample after removing labeled PNA with complementary PNA immobilized on bead (E).
Figure 9B:
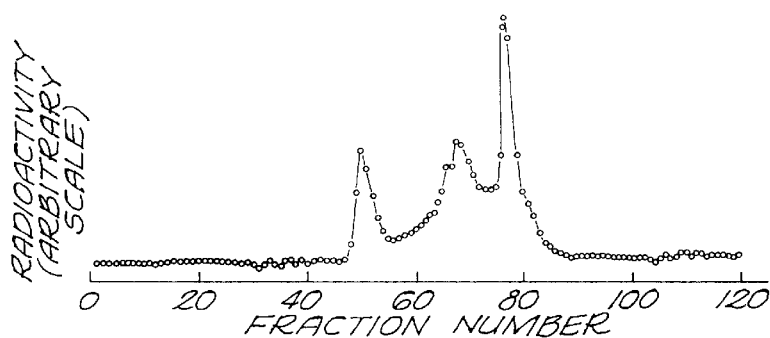
Figure 9C:
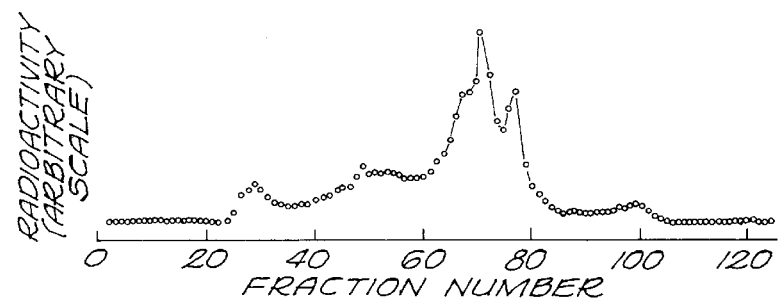
Figure 9D:
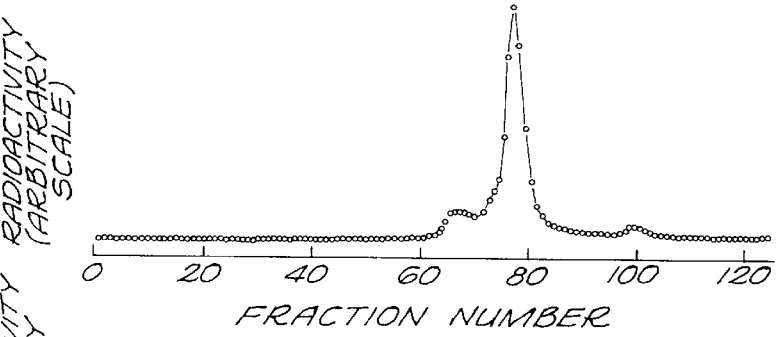
Figure 9E:
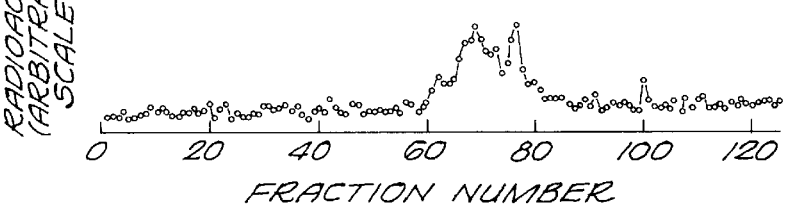

FIG. 9A presents HPLC radiochromatograms of labeled PNA administered to normal mice. The figure also shows the results of analyzing the serum (FIG. 9B) and urine samples (FIG. 9D) obtained at 2.5 hrs post administration. The serum sample shows only a single radiolabeled serum peak while the urine sample shows one of the labeled PNA peaks. FIG. 9E is a repeat radiochromatogram (now presented on an expanded scale) obtained by analyzing the urine after the addition of complementary PNA beads. Virtually all radioactivity has been removed showing that the label in urine is present as labeled PNA. FIG. 9C presents a radiochromatogram of the soluble fraction from the homogenate of a kidney obtained at this time showing labeled PNA and higher molecular weight, presumably labeled proteins. However, this analysis considers only about 20% of the radiolabel in the kidney since the remainder appeared in the insoluble pellet.

EXAMPLE 12
Animal Biodistribution and Imaging Studies

Biodistributions of technetium-99m-MAG$_3$-PNA were evaluated in normal CD-1 male mice. Each animal was administered by tail vein 0.1 milliliters of 0.15M saline containing 5 micrograms (about 100 microCuries) of technetium-99m-MAG$_3$-PNA. Whole body activity was determined by repeatedly placing each animal momentarily in a dose calibrator. The anesthetized animals were sacrificed by spinal dislocation at 2.5 and 24 hrs post administration. Samples of organs were rinsed in cold saline and were weighed before being counted in a NaI(Tl) well counter along with a blood sample and an aliquot of the injectate The biodistributions were reported as percent of the administered radioactivity per gram of tissue.

In a separate study, three male CD-1 mice were each injected intramuscularly in their left thighs with 150 milliliters of saline containing 1.0 milligrams of PNA-coupled beads. An exact equivalent of beads without PNA was injected into their contralateral thighs. Immediately thereafter, each animal received an intraperitoneal injection of 50–55 micrograms (about 1 milliCurie) of labeled PNA. Animals were imaged simultaneously on an Elscint APEX 409M portable gamma camera by resting the nembutal-anesthetized animals on the face of the upright collimator. Animals were imaged five times between 2 and 23 hrs post administration of the labeled PNA. At sacrifice, both whole thighs were excised for counting in a NaI(Tl) well counter. Regions of interest were drawn about the thighs and whole body in each image to obtain an estimate of the counts therein. Based on the counts in each image, the well counter counts of the thigh and the injected activity, the percent of the injected dosage in each thigh at each time point was estimated. The left thigh/whole body radioactivity ratios were calculated without correction simply from the counts in each image.

Figure 10:
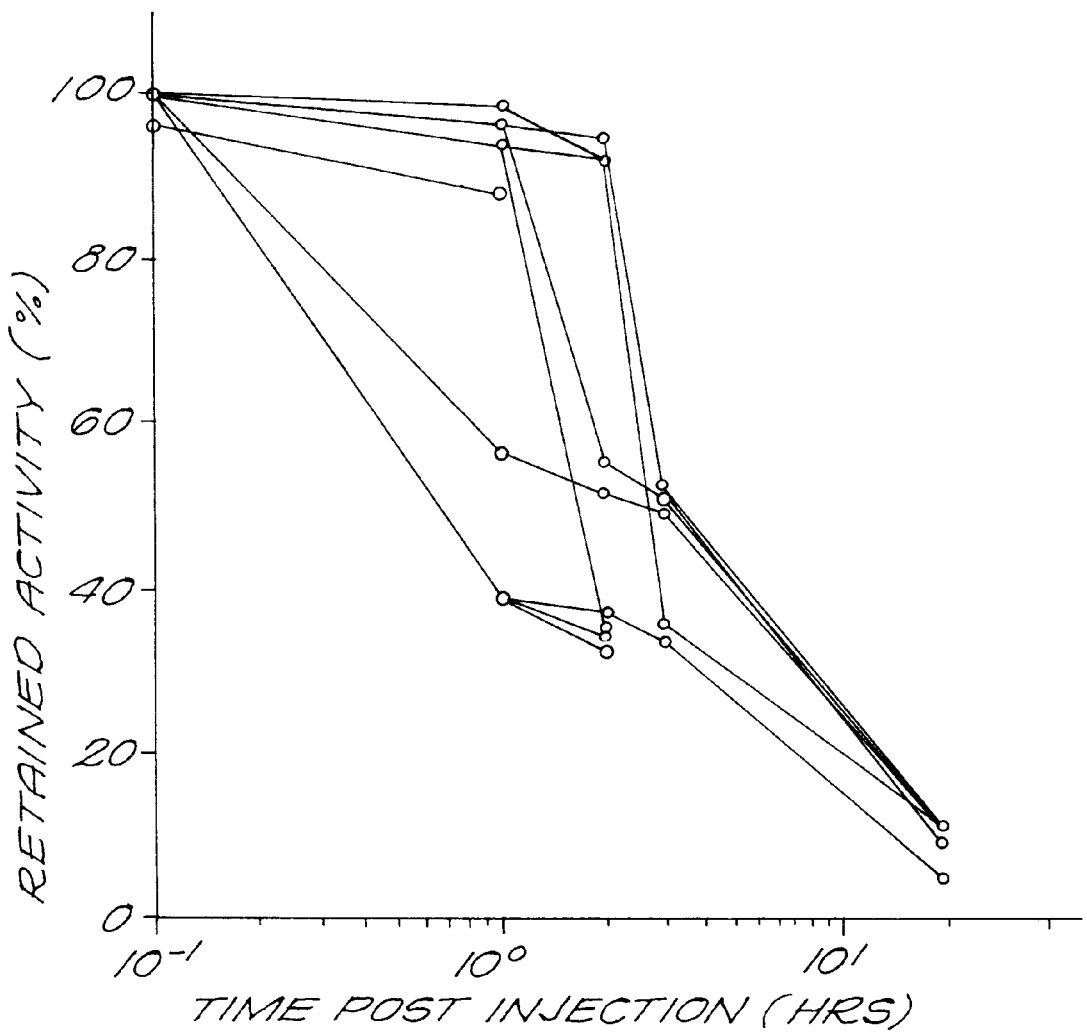
FIG. 10 shows whole body radioactivity as a function of time (each of the experimental animals plotted as a different symbol) following injection of radiolabeled PNA.

FIG. 10 shows the whole body radioactivity plotted separately for each of ten mice receiving 5 micrograms each of labeled PNA. The half time of clearance is approximately 2 hrs.

TABLE 1

Table 1 shows the mean biodistribution (in percentage injected dose/milligrams of tissue) obtained in normal mice at times of 2.5 hrs. and 24 hrs. post intraperitoneal administration of technetium-99m-labeled-MAG$_3$-PNA. The data are the mean of values from five experimental animals, with standard deviation in parenthesis

| Organ | 2.5 hrs. | 24 hrs. |
| --- | --- | --- |
| Liver | 0.19(0.08) | 0.010(0.002) |
| Heart | 0.05(0.03) | 0.001(0.002) |
| Kidneys | 1.45(0.88) | 0.065(0.017) |
| Lung | 0.11(0.05) | 0.002(0.001) |
| Stomach | 1.30(0.82) | 0.050(0.027) |
| Spleen | 0.05(0.02) | 0.000(0.001) |
| Muscle | 0.06(0.04) | 0.001(0.002) |
| Intestine | 0.18(0.11) | 0.007(0.004) |
| Blood | 0.17(0.07) | 0.000(0.000) |

Table 1 presents the biodistribution results obtained at 2.5 and 24 hrs post administration of the radiolabeled PNA. The results reflect the rapid clearance of the label shown in FIG. 10; the highest radioactive content is only 1.45% of the injected dose per gram (ID/gm) at 2.5 hrs and 0.07% ID/gm at 24 hrs (in both cases in kidneys).

Figure 11:
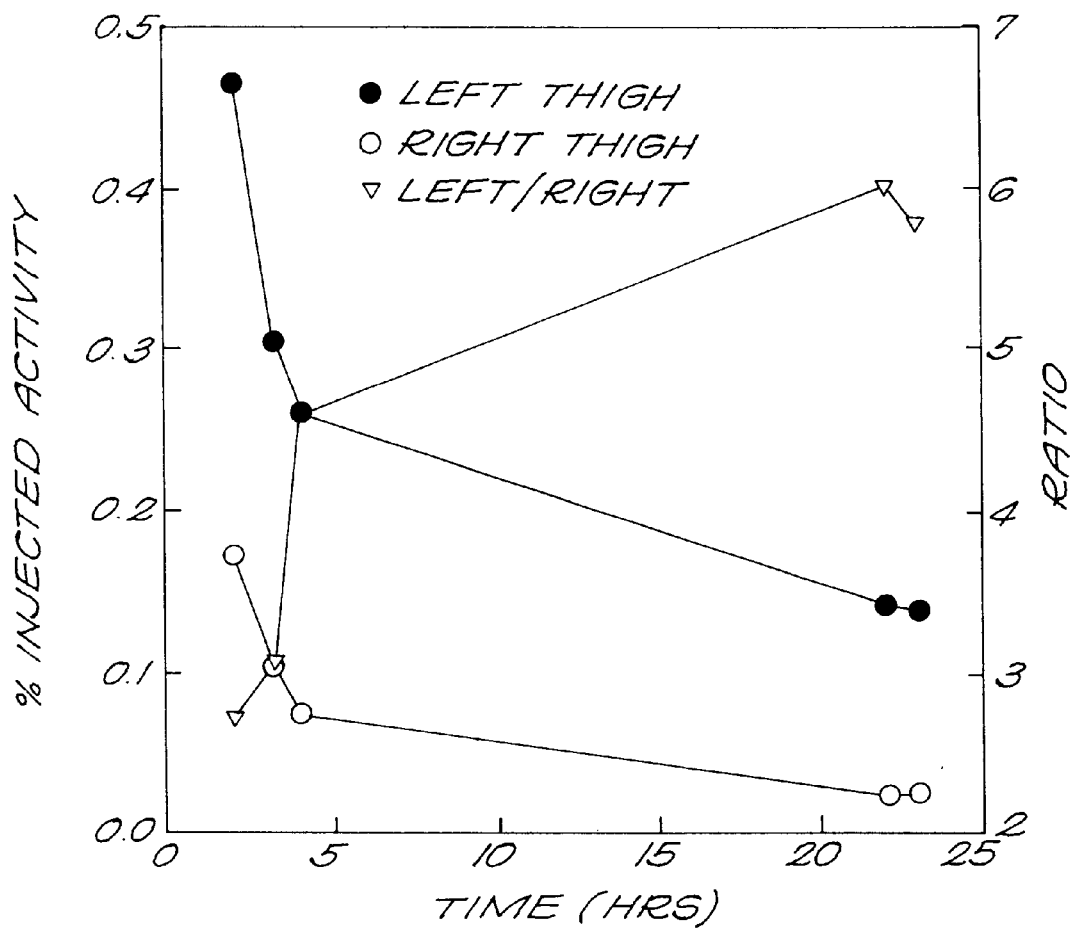
FIG. 11 shows the percentage of injected radioactivity in the left thigh (closed circles) and right thigh (open circles) as a function of time after administration of labeled PNA to mice implanted with complementary PNA-containing beads in the left thigh (left scale), and the left/right thigh radioactivity ratio as a function of time (inverted triangles, right scale).

Three animals received identical administrations of beads subcutaneously in both thighs prior to the IP administration of the labeled PNA. In all cases, only the beads in the left thigh contained the complementary PNA. FIG. 11 presents the mean percentage of injected radioactivity in the left and right thighs along with the left/right thigh radioactivity ratios at each time point. The left thigh/whole body ratio rose from 0.05 at 2 hours to 0.09 at 23 hours post injection. As is evident from the figure, the left/right thigh radioactivity ratio rose from 2.7 to 5.8 during this period. A composite whole body anterior-posterior image of the three animals imaged simultaneously at 23 hrs post administration shows radioactivity essentially only in kidneys, bladder, and the left thigh. These data and the left/right thigh radioactivity demonstrate in vivo hybridization of PNA-MAG$_3$-radionuclide to its complement.

For use in radiopharmaceutical applications, oligomers must possess certain essential properties. Since diagnostic applications require only tracer quantities of drug, toxicity is unlikely to be an issue. Among other considerations, suitable stability of the oligomer in vivo is also essential. In addition, the pharmacokinetic properties must be suitable for the intended application. For example, the oligomer should clear through the kidneys in a time frame consistent with the application to provide a favorable target/nontarget ratio. For use as radiopharmaceuticals, it must be possible to radiolabel with imagable radionuclides such as technetium-99m and that the label be suitably stable in vivo. Finally, the labeled oligomer must be capable of hybridization in vivo with its complement in the target.

Although the in vivo properties were influenced to some extent by the method of radiolabeling, the phosphodiester DNA was judged to be degraded by nucleases too rapidly for most applications. The phosphorothioate DNA, although stable towards nuclease digestion, showed a high affinity for serum and tissue proteins. As a consequence, background radioactivity in liver and other tissues was present at unacceptably high levels.

Peptide nucleic acids are synthetic oligomers in which the sugar and phosphate backbone of oligonucleotides have been replaced with a polyamide linkage. Not only does this substitution provide an oligomer resistant to nuclease and protease attack, but the absence of charge improves the binding affinity of PNA-DNA heteroduplexes.

In these examples, radiolabeling with technetium-99m was achieved by means of an acetyl-protected MAG$_3$ chelator. This labeling strategy was developed to avoid "nonspecific" serum protein binding observed for DNA labeled using a hydrazino nicotinamide (SHNH) chelator. Similar properties for technetium-99m in vitro and in vivo are seen in animals when labeled to two IgG antibodies by MAG$_3$ and SHNH chelators (data not shown). Using MAG$_3$, respectable labeling efficiencies and specific activities were achieved for PNA. Furthermore, the stability of the label in 37° C. serum was acceptable with minimal activity present on either higher or lower molecular weight species (FIG. 7).

Although a UV profile of PNA showed a single peak by HPLC analysis (data not presented), the radioactivity profiles always consisted of two to three distinct peaks with only the earliest eluting with UV absorbency. Furthermore, the HPLC radioactivity profile varied somewhat from preparation to preparation but showed a consistent and profound shift to the third (i.e. last) peak on incubation in saline and, especially, in serum (FIGS. 7,8). That all three peaks were radiolabeled PNA was established by demonstrating that each shifted to higher molecular weight upon addition of the complementary PNA (FIG. 5). Thus, the radionuclide is maintained in the complex with PNA.

It has been reported that PNA undergoes negligible transport across cell membranes (Pardrige W M., Boado R J., Kang Y-S. *Proc Natl Acad Sci USA* 92: 5592–5596; et.al. 1995). Support for this property of technetium-99m-MAG$_3$-PNA may be found in the negligible accumulation of radiolabel in formed elements following incubation of labeled PNA in whole blood.

These examples teach that the properties of PNA labeled according to the methods used herein are suitable for imaging studies in vivo. Apart from the stability of the label discussed above, the pharmacokinetic properties are favorable. Whole body radioactivity in mice following IV administration showed a rapid decrease (FIG. 9). The biodistribution studies in normal mice (Table 1) also showed this rapid decrease. At 2.5 hrs., the highest level of radioactivity was in kidneys at only 1.45% ID/gm. At 24 hrs, radioactivity in several tissues were below detectability. These results are in sharp contrast to that observed in this laboratory for technetium-99m-labeled phosphodiester and phosphorothioate DNAs of about the same chain length where tissue radioactivity levels (except for stomach) at 4 hrs post-administration were about 2–10 times higher for the phosphodiester DNA and 10–400 times higher for the phosphorothioate DNA incorporated here by reference. As shown (FIG. 8), hybridization under one set of conditions is more than 50% complete in less than 10 min.

A test of suitability for medical use of oligomers may be in vivo hybridization. Only in the left thigh were the implanted beads first bound with the complementary PNA. Following intraperitoneal administration of radiolabeled PNA, increased accumulation of label occurred in the left thigh due to hybridization, with the left/right radioactivity ratio increasing with time between 2 and 23 hrs. Apart from radioactivity in the left thigh, the whole body image show radioactivity only in bladder and kidneys.

These data demonstrate that single stranded PNA may be radiolabeled with technetium-99m using the MAG$_3$ chelator. Importantly, when administered to mice, radiolabeled PNA can be made to hybridize in vivo.

Those skilled in the art will recognize, or be able to ascertain using no more than routine experimentation, numerous equivalents to the specific procedures described herein. Such equivalents are considered to be within the scope of this invention and are covered by the following claims.

The contents of all patents and publications referred to herein are hereby incorporated by reference.

Other embodiments are within the following claims.

What is claimed is:

1. A method of forming a polymer-chelator-radionuclide complex under mild conditions, comprising the steps of
   (a) contacting a polymer-chelator compound with a radionuclide in the presence of a reducing agent, and
   (b) allowing a polymer-chelator-radionuclide complex to form under mild conditions,
   wherein the polymer-chelator compound comprises a polymer coupled to a tetradentate mercaptooligopeptide chelator moiety, the chelator moiety comprises a sulfur atom protected by a protecting group of the formula —C(O)-lower alkyl, and the polymer-chelator compound is selected from the group consisting of protein-chelators and nucleic acid-chelators.

2. The method of claim 1, wherein the radionuclide is technetium-99m.

3. The method of claim 2, wherein the technetium-99m is provided in the form of a pertechnetate.

4. The method of claim 3, wherein the method comprises further contacting the pertechnetate with a reducing agent.

5. A kit comprising a polymer-chelator compound in a container, wherein the polymer-chelator compound comprises a polymer linked to a chelator moiety, and the chelator moiety comprises an oligopeptide having residues selected from the group consisting of serine, proline, alanine, and phenylalanine and a sulfur atom protected by a protecting group of the formula —C(O)-lower alkyl and is linked to the polymer moiety through an amide or an ester bond, and instructions for complexing the polymer-chelator compound with a radionuclide under mild conditions.

6. The kit of claim 5, wherein the polymer-chelator compound is an antibody-chelator.

7. A method of claim 1, wherein the mercaptooligopeptide chelator moiety consists essentially of amino acids selected from the group consisting of serine, proline, alanine, and phenylalanine.

8. A composition comprising acetyl-N-[N-[N-mercaptoacetyl]-seryl]seryl]serine.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 22 bases
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: synthetic polydeoxyribonucleic acid
         complementary to SEQ ID NO:2

(xi) SEQUENCE DESCRIPTION: SEQ ID NO:1:

TAATACGACT CACTATAGGG AG                                  22

(2) INFORMATION FOR SEQ ID NO:2:

(i) SEQUENCE CHARACTERISTICS:
      (A) LENGTH: 22 bases
      (B) TYPE: nucleic acid
      (C) STRANDEDNESS: single
      (D) TOPOLOGY: linear

```
        (ii) MOLECULE TYPE: DNA (ix) FEATURE:
                (D) OTHER INFORMATION:synthetic polydeoxyribonucleic acid
                    complementary to SEQ ID NO:1

(xi) SEQUENCE DESCRIPTION: SEQ ID NO:2:

CTCCCTATAG TGAGTCGTAT TA                                                22

(2) INFORMATION FOR SEQ ID NO:3:

(i) SEQUENCE CHARACTERISTICS:
                (A) LENGTH: 15 bases
                (B) TYPE: nucleic acid
                (C) STRANDEDNESS: single
                (D) TOPOLOGY: linear (ii) MOLECULE TYPE: other nucleic acid (ix) FEATURE:
                (D) OTHER INFORMATION: synthetic peptide nucleic acid
                    complementary to SEQ ID NO:4

(xi) SEQUENCE DESCRIPTION: SEQ ID NO:3:

TGTACGTCAC AACTA                                                        15

(2) INFORMATION FOR SEQ ID NO:4:

(i) SEQUENCE CHARACTERISTICS:
                (A) LENGTH: 15 bases
                (B) TYPE: nucleic acid
                (C) STRANDEDNESS: single
                (D) TOPOLOGY: linear (ii) MOLECULE TYPE: other nucleic acid (ix) FEATURE:
                (D) OTHER INFORMATION: synthetic peptide nucleic acid
                    complementary to SEQ ID NO:3

(xi) SEQUENCE DESCRIPTION: SEQ ID NO:4:

TAGTTGTGAC GTACA                                                        15
```